(12) United States Patent
Stahmann et al.

(10) Patent No.: US 7,979,115 B2
(45) Date of Patent: *Jul. 12, 2011

(54) DETECTION OF PLEURAL EFFUSION USING TRANSTHORACIC IMPEDANCE

(75) Inventors: Jeffrey E. Stahmann, Ramsey, MN (US); John Hatlestad, Maplewood, MN (US); Jesse W. Hartley, Lino Lakes, MN (US); Richard Fogoros, Pittsburg, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 218 days.

This patent is subject to a terminal disclaimer.

(21) Appl. No.: 11/972,405

(22) Filed: Jan. 10, 2008

(65) Prior Publication Data

US 2008/0108907 A1 May 8, 2008

Related U.S. Application Data

(63) Continuation of application No. 11/132,109, filed on May 18, 2005, now Pat. No. 7,340,296.

(51) Int. Cl.
*A61B 5/05* (2006.01)
(52) U.S. Cl. ....................................... 600/547
(58) Field of Classification Search ................. 600/547, 600/386, 538, 529; 607/17, 9
See application file for complete search history.

(56) References Cited

U.S. PATENT DOCUMENTS

| | | | |
|---|---|---|---|
| 3,340,867 A | 9/1967 | Kubicek et al. | |
| 3,871,359 A | 3/1975 | Pacela | |
| 4,003,379 A | 1/1977 | Ellinwood, Jr. | |
| 4,059,169 A | 11/1977 | Hagen | |
| RE30,101 E | 9/1979 | Kubicek et al. | |
| 4,271,192 A | 6/1981 | Wurtman et al. | |
| 4,437,469 A | 3/1984 | Djordjevich et al. | |
| 4,450,527 A | 5/1984 | Sramek | |

(Continued)

FOREIGN PATENT DOCUMENTS

EP 348271 12/1989

(Continued)

OTHER PUBLICATIONS

"Heart Sounds", [online]. [retrieved on Dec. 8, 2005]. Retrieved from the Internet: <URL: http://www.chfpatients.com/faq/s3s4.htm>, 4 pgs.

(Continued)

*Primary Examiner* — Max Hindenburg
*Assistant Examiner* — Fangemonique Smith
(74) *Attorney, Agent, or Firm* — Schwegman, Lundberg & Woessner, P.A.

(57) ABSTRACT

This patent document discusses systems, devices, and methods for increasing a sensitivity or specificity of thoracic fluid detection in a subject and differentiating between pleural effusion and pulmonary edema. In one example, a thoracic impedance measurement circuit senses a thoracic impedance signal. In another example, a processor receives the thoracic impedance signal and determines whether such thoracic impedance signal is "significant." A significant thoracic impedance signal indicates the presence of thoracic fluid and may be recognized by comparing the thoracic impedance signal (or variation thereof) to a thoracic impedance threshold. When a significant thoracic impedance signal is recognized, the processor is adapted to detect one or both of: a pleural effusion indication and a pulmonary edema indication using one or a combination of: physiologic information, patient symptom information, and posture information. In another example, the thoracic impedance threshold is adjusted using such physiologic, patient symptom, or posture information.

21 Claims, 7 Drawing Sheets

U.S. PATENT DOCUMENTS

| | | | |
|---|---|---|---|
| 4,470,987 A | 9/1984 | Wurtman et al. | |
| 4,472,420 A | 9/1984 | Toth | |
| 4,472,431 A | 9/1984 | Toth | |
| 4,559,946 A | 12/1985 | Mower | |
| 4,562,843 A | 1/1986 | Djordjevich et al. | |
| 4,567,892 A | 2/1986 | Plicchi et al. | |
| 4,576,183 A | 3/1986 | Plicchi et al. | |
| 4,651,716 A | 3/1987 | Forester et al. | |
| 4,686,987 A | 8/1987 | Salo et al. | |
| 4,693,253 A | 9/1987 | Adams | |
| 4,880,005 A | 11/1989 | Pless et al. | |
| 4,884,576 A | 12/1989 | Alt | |
| 4,904,472 A | 2/1990 | Belardinelli et al. | |
| 4,919,136 A | 4/1990 | Alt | |
| 4,980,379 A | 12/1990 | Belardinelli et al. | |
| 4,987,897 A | 1/1991 | Funke | |
| 5,002,052 A | 3/1991 | Haluska | |
| 5,003,976 A | 4/1991 | Alt | |
| 5,025,786 A | 6/1991 | Siegel | |
| 5,031,629 A | 7/1991 | DeMarzo | |
| 5,036,849 A | 8/1991 | Hauck et al. | |
| 5,113,869 A | 5/1992 | Nappholz et al. | |
| 5,117,825 A | 6/1992 | Grevious | |
| 5,178,154 A | 1/1993 | Ackmann et al. | |
| 5,179,947 A | 1/1993 | Meyerson et al. | |
| 5,199,428 A | 4/1993 | Obel et al. | |
| 5,213,098 A | 5/1993 | Bennett et al. | |
| 5,215,083 A | 6/1993 | Drane et al. | |
| 5,233,985 A | 8/1993 | Hudrlik | |
| 5,246,008 A | 9/1993 | Mueller | |
| 5,271,395 A | 12/1993 | Wahlstrand et al. | |
| 5,273,034 A | 12/1993 | Nilsson | |
| 5,282,836 A | 2/1994 | Kreyenhagen et al. | |
| 5,282,840 A | 2/1994 | Hudrlik | |
| 5,284,136 A | 2/1994 | Hauck et al. | |
| 5,292,343 A | 3/1994 | Blanchette et al. | |
| 5,300,093 A | 4/1994 | Koestner et al. | |
| 5,309,917 A | 5/1994 | Wang et al. | |
| 5,313,953 A | 5/1994 | Yomtov et al. | |
| 5,324,309 A | 6/1994 | Kallok | |
| 5,324,315 A | 6/1994 | Grevious | |
| 5,344,429 A | 9/1994 | Smits | |
| 5,354,317 A | 10/1994 | Alt | |
| 5,354,319 A | 10/1994 | Wyborny et al. | |
| 5,355,894 A | 10/1994 | Sivard | |
| 5,366,485 A | 11/1994 | Kroll et al. | |
| 5,370,665 A | 12/1994 | Hudrlik | |
| 5,391,190 A | 2/1995 | Pederson et al. | |
| 5,404,877 A | 4/1995 | Nolan et al. | |
| 5,405,362 A | 4/1995 | Kramer et al. | |
| 5,411,031 A | 5/1995 | Yomtov | |
| 5,431,682 A | 7/1995 | Hedberg | |
| 5,441,525 A | 8/1995 | Shelton et al. | |
| 5,443,073 A | 8/1995 | Wang et al. | |
| 5,454,377 A | 10/1995 | Dzwonczyk et al. | |
| 5,464,434 A | 11/1995 | Alt | |
| 5,479,369 A | 12/1995 | Matsumura et al. | |
| 5,484,401 A * | 1/1996 | Rodriguez et al. | 604/28 |
| 5,501,701 A | 3/1996 | Markowitz et al. | |
| 5,505,209 A | 4/1996 | Reining | |
| 5,507,785 A | 4/1996 | Deno | |
| 5,522,860 A | 6/1996 | Molin et al. | |
| 5,526,808 A | 6/1996 | Kaminsky | |
| 5,534,018 A | 7/1996 | Wahlstrand et al. | |
| 5,540,728 A | 7/1996 | Shelton et al. | |
| 5,562,711 A | 10/1996 | Yerich et al. | |
| 5,562,712 A | 10/1996 | Steinhaus et al. | |
| 5,626,623 A | 5/1997 | Kieval et al. | |
| 5,642,734 A | 7/1997 | Ruben et al. | |
| 5,676,686 A | 10/1997 | Jensen et al. | |
| 5,685,316 A | 11/1997 | Schookin et al. | |
| 5,706,829 A | 1/1998 | Kadri | |
| 5,722,999 A | 3/1998 | Snell | |
| 5,725,561 A | 3/1998 | Stroebel et al. | |
| 5,725,562 A | 3/1998 | Sheldon | |
| 5,732,710 A | 3/1998 | Rabinovich et al. | |
| 5,735,284 A | 4/1998 | Tsoglin et al. | |
| 5,749,369 A | 5/1998 | Rabinovich et al. | |
| 5,749,900 A | 5/1998 | Schroeppel et al. | |
| 5,782,774 A | 7/1998 | Shmulewitz | |
| 5,782,879 A | 7/1998 | Rosborough et al. | |
| 5,782,884 A | 7/1998 | Stotts et al. | |
| 5,788,643 A | 8/1998 | Feldman | |
| 5,791,349 A | 8/1998 | Shmulewitz | |
| 5,800,464 A | 9/1998 | Kieval | |
| 5,824,029 A | 10/1998 | Weijand et al. | |
| 5,865,760 A | 2/1999 | Lidman et al. | |
| 5,874,420 A | 2/1999 | Pelleg | |
| 5,876,353 A | 3/1999 | Riff | |
| 5,913,879 A | 6/1999 | Ferek-Petric et al. | |
| 5,919,210 A | 7/1999 | Lurie et al. | |
| 5,957,861 A | 9/1999 | Combs et al. | |
| 5,957,957 A | 9/1999 | Sheldon | |
| 5,974,340 A | 10/1999 | Kadhiresan | |
| 5,978,705 A | 11/1999 | KenKnight et al. | |
| 6,026,324 A | 2/2000 | Carlson | |
| 6,035,233 A | 3/2000 | Schroeppel et al. | |
| 6,044,297 A | 3/2000 | Sheldon et al. | |
| 6,049,735 A | 4/2000 | Hartley et al. | |
| 6,075,015 A | 6/2000 | Sestelo et al. | |
| 6,076,015 A | 6/2000 | Hartley et al. | |
| 6,078,834 A | 6/2000 | Lurie et al. | |
| 6,095,987 A | 8/2000 | Shmulewitz et al. | |
| 6,104,949 A * | 8/2000 | Pitts Crick et al. | 600/547 |
| 6,154,672 A | 11/2000 | Pendekanti et al. | |
| 6,161,038 A | 12/2000 | Schookin et al. | |
| 6,186,955 B1 | 2/2001 | Baura | |
| 6,228,033 B1 | 5/2001 | Koobi et al. | |
| 6,292,689 B1 | 9/2001 | Wallace et al. | |
| 6,298,267 B1 | 10/2001 | Rosborough et al. | |
| 6,314,322 B1 | 11/2001 | Rosenberg | |
| 6,317,631 B1 | 11/2001 | Ben-Haim et al. | |
| 6,336,903 B1 | 1/2002 | Bardy | |
| 6,411,844 B1 | 6/2002 | Kroll et al. | |
| 6,438,408 B1 | 8/2002 | Mulligan et al. | |
| 6,473,640 B1 | 10/2002 | Erlebacher | |
| 6,511,438 B2 | 1/2003 | Bernstein et al. | |
| 6,512,949 B1 | 1/2003 | Combs et al. | |
| 6,560,481 B1 | 5/2003 | Heethaar et al. | |
| 6,561,986 B2 | 5/2003 | Baura et al. | |
| 6,574,506 B2 | 6/2003 | Kramer et al. | |
| 6,595,927 B2 * | 7/2003 | Pitts-Crick et al. | 600/529 |
| 6,600,949 B1 | 7/2003 | Turcott | |
| 6,602,201 B1 | 8/2003 | Hepp et al. | |
| 6,625,492 B2 | 9/2003 | Florio et al. | |
| 6,636,754 B1 | 10/2003 | Baura et al. | |
| 6,643,543 B2 | 11/2003 | Takehara et al. | |
| 6,665,564 B2 | 12/2003 | Lincoln et al. | |
| 6,678,547 B2 | 1/2004 | Carlson et al. | |
| 6,714,813 B2 | 3/2004 | Ishigooka et al. | |
| 6,748,271 B2 | 6/2004 | Spinelli et al. | |
| 6,752,765 B1 | 6/2004 | Jensen et al. | |
| 6,811,537 B2 | 11/2004 | Bardy | |
| 6,829,503 B2 | 12/2004 | Alt | |
| 6,907,288 B2 | 6/2005 | Daum | |
| 6,908,437 B2 | 6/2005 | Bardy | |
| 6,912,420 B2 | 6/2005 | Scheiner et al. | |
| 7,003,346 B2 | 2/2006 | Singer | |
| 7,149,573 B2 | 12/2006 | Wang | |
| 7,177,681 B2 | 2/2007 | Zhu et al. | |
| 7,191,000 B2 | 3/2007 | Zhu et al. | |
| 7,340,296 B2 | 3/2008 | Stahmann et al. | |
| 7,387,610 B2 | 6/2008 | Stahmann et al. | |
| 7,672,718 B2 | 3/2010 | Stahmann et al. | |
| 2001/0020138 A1 | 9/2001 | Ishigooka et al. | |
| 2002/0115939 A1 | 8/2002 | Mulligan et al. | |
| 2002/0123674 A1 | 9/2002 | Plicchi et al. | |
| 2002/0138014 A1 | 9/2002 | Baura et al. | |
| 2002/0147475 A1 | 10/2002 | Scheiner et al. | |
| 2002/0147476 A1 | 10/2002 | Daum | |
| 2002/0193689 A1 | 12/2002 | Bernstein et al. | |
| 2003/0023279 A1 | 1/2003 | Spinelli et al. | |
| 2003/0028221 A1 | 2/2003 | Zhu et al. | |
| 2003/0055461 A1 | 3/2003 | Girouard et al. | |
| 2003/0074029 A1 | 4/2003 | Deno et al. | |
| 2003/0105496 A1 | 6/2003 | Yu et al. | |
| 2003/0139679 A1 | 7/2003 | Kushnir et al. | |

| | | | |
|---|---|---|---|
| 2003/0176896 A1 | 9/2003 | Lincoln et al. | |
| 2003/0191503 A1 | 10/2003 | Zhu et al. | |
| 2003/0220580 A1 | 11/2003 | Alt | |
| 2004/0049235 A1* | 3/2004 | Deno et al. | 607/9 |
| 2004/0073128 A1 | 4/2004 | Hatlestad et al. | |
| 2004/0073262 A1 | 4/2004 | Lovett | |
| 2004/0086864 A1 | 5/2004 | Lo et al. | |
| 2004/0102712 A1 | 5/2004 | Belalcazar et al. | |
| 2004/0116819 A1 | 6/2004 | Alt | |
| 2004/0127807 A1 | 7/2004 | Hatlesad et al. | |
| 2004/0133079 A1 | 7/2004 | Mazar et al. | |
| 2004/0147982 A1 | 7/2004 | Bardy | |
| 2004/0172080 A1 | 9/2004 | Stadler et al. | |
| 2004/0215097 A1 | 10/2004 | Wang | |
| 2004/0215270 A1 | 10/2004 | Ritscher et al. | |
| 2005/0004609 A1 | 1/2005 | Stahmann et al. | |
| 2005/0021098 A1 | 1/2005 | Spinelli et al. | |
| 2005/0043675 A1 | 2/2005 | Pastore et al. | |
| 2005/0080460 A1 | 4/2005 | Wang et al. | |
| 2005/0124908 A1* | 6/2005 | Belalcazar et al. | 600/547 |
| 2005/0137480 A1 | 6/2005 | Alt et al. | |
| 2005/0177062 A1 | 8/2005 | Skrabal et al. | |
| 2005/0283197 A1 | 12/2005 | Daum et al. | |
| 2005/0288721 A1 | 12/2005 | Girouard et al. | |
| 2006/0041280 A1 | 2/2006 | Stahmann et al. | |
| 2006/0134071 A1 | 6/2006 | Ross et al. | |
| 2006/0134079 A1 | 6/2006 | Sih et al. | |
| 2006/0135886 A1 | 6/2006 | Lippert et al. | |
| 2006/0241512 A1 | 10/2006 | Kwok et al. | |
| 2006/0241513 A1 | 10/2006 | Hatlestad et al. | |
| 2006/0258952 A1 | 11/2006 | Stahmann et al. | |
| 2006/0264776 A1 | 11/2006 | Stahmann et al. | |
| 2006/0293609 A1 | 12/2006 | Stahmann et al. | |
| 2007/0054871 A1 | 3/2007 | Pastore et al. | |
| 2008/0249433 A1 | 10/2008 | Stahmann et al. | |
| 2010/0076336 A1 | 3/2010 | Stahmann | |

FOREIGN PATENT DOCUMENTS

| | | |
|---|---|---|
| EP | 0584388 A1 | 3/1994 |
| EP | 0620420 | 10/1994 |
| EP | 0663219 A1 | 7/1995 |
| EP | 1057498 | 12/2000 |
| EP | 1078597 | 2/2001 |
| EP | 606301 | 12/2001 |
| EP | 1247487 | 10/2002 |
| EP | 1275342 | 1/2003 |
| EP | 771172 | 4/2003 |
| WO | WO-84/00227 | 1/1984 |
| WO | WO-93/04627 | 3/1993 |
| WO | WO-96/01586 | 1/1996 |
| WO | WO-97/37591 | 10/1997 |
| WO | WO-97/38628 | 10/1997 |
| WO | WO 98/51211 | 11/1998 |
| WO | WO-01/41638 | 6/2001 |
| WO | WO-02/053026 | 7/2002 |
| WO | WO-02/053228 | 7/2002 |
| WO | WO-03/020364 | 3/2003 |

OTHER PUBLICATIONS

"Medtronic Announces European Release of Innovative InSync Sentry Cardiac Resynchronization Therapy Defibrillator", [online]. http://www.medtronic.com/newsroom/news_20040614a.html, (2004), 2pgs.

"Medtronic: Insync Sentry™ 7298", www.medtronic.com, Reference Manual,(2004), 420 pgs.

Adamicza, A. , et al., "Changes in transthoracic electrical impedance during endotoxemia in dogs", *Acta Physiol Hung.*, 85(4), (1997-1998),291-302.

Adamicza, A. , et al., "Investigation of the thoracic electrical impedance during endotoxemia in dogs", *Acta Chir Hung.*, 36(1-4), (1997),1-3.

Alt, Eckhard, et al., "Control of Pacemaker Rate by Impedance-based Respiratory Minute Ventilation", *Chest*, 92(2), (Aug. 1987),247-252.

Baarends, E. M., et al., "Body-water compartments measured by bio-electrical impedance spectroscopy in patients with chronic obstructive pulmonary disease", *Clinical Nutrition*, 17(1), (Feb. 1998),15-22.

Belalcazar, Andres , et al., "Improved lung edema monitoring with coronary vein pacing leads", *Pacing and Clinical Electrophysiology*, 26(4 pt. II), Abstract 18,(Apr. 2003),933.

Belalcazar, Andres , et al., "Improved lung edema monitoring with coronary vein pacing leads: a simulation study", *Physiological Measurement*, vol. 25, (2004),475-487.

Berman, Irwin R., et al., "Transthoracic electrical impedance s a guide to intravascular overload", *Archives of Surgery*, 102(1), (Jan. 1971),61-64.

Bradbury, M. G., et al., "Assessment of the sensitivity of bioimpedance to volume changes in body water", *Pediatr Nephrol.*, 9(3), (Jun. 1995),337-340.

Campbell, J. H., et al., "Clinical applications of electrical impedance tomography in the monitoring of changes in intrathoracic fluid volumes", *Physiol. Meas.*, vol. 15, (1994),A217-A222.

Campbell, J. H., et al., "Detection of changes in intrathoracic fluid in man using electrical impedance tomography", *Clinical Science*, vol. 87, (1994),97-101.

Charach, Gideon , et al., "Transthoracic monitoring of the impedance of the right lung in patients with cardiogenic pulmonary edema", *Critical Care Medicine*, 29(6), (Jun. 2001),1137-44.

Chiolero, R. L., "Assessment of changes in body water by bioimpedance in acutely ill surgical patients.", *Intensive Care Medicine*, 18(6), (1992),322-6.

Defaye, P. , et al., "Automatic Recognition of Abnormal Respiratory Events During Sleep by a Pacemaker Transthoracic Impedance Sensor", *Journal of Cardiovascular Electrophysiology*, 15(9), (Sep. 2004),1034-40.

Denniston, J. C., et al., "Factors Influencing the measurement of stroke volume by electrical impedence", *Physiology* (1372-1377), Abstract No. 1373,463.

Denniston, J. C., et al., "Measurement of pleural effusion by electrical impedance.", *Journal of Applied Physiology*, 38(5), (May 1975),851-7.

Ebert, T J., et al., "The use of thoracic impedance for determining thoracic blood volume changes in man", *Aviat Space Environ Med.*, 57(1), (Jan. 1986),49-53.

Ellenbogen, Kenneth A., et al., "Rate-adaptive pacing based on impedance-derived minute ventilation", *Clinical Cardiac Pacing*, Philadelphia : Saunders,(1995),219-233.

Ellenbogen, Kenneth A., et al., "The Electrode-Tissue Interface and the Foreign Body Response", *Clinical Cardiac Pacing*, Philadelphia :Saunders,(1995),22-23.

Fein, Alan , et al., "Evaluation of Transthoracic Electrical Impedance in the Diagnosis of Pulmonary Edema", *Circulation*, 60(5), (Nov. 1979),1156-1160.

Fleischhauer, J. , et al., "Electrical resistances of interstitial and microvascular space as determinants of the extracellular electrical field and velocity of propagation in ventricular myocardium", *Circulation*, (Aug. 1, 1995),587-594.

Foreman, B , et al., "Intra-thoracic impedance: a surrogate measure of thoracic fluid—fluid accumulation status trial (FAST)", *Journal of Cardiac Failure*, 10(4 Suppl), Abstract 251,(2004),S86.

Forro, M. , et al., "Total body water and ECFV measured using bioelectrical impedance analysis and indicator dilution in horses", *Journal of Applied Physiology*, 89(2), (Aug. 2000),663-71.

Frerichs, I. , et al., "Electrical impedance tomography in monitoring experimental lung injury", *Intensive Care Med.*, 24(8), (Aug. 1998),829-36.

Garland, J. S., et al., "Measurement of extravascular lung water in hemodialysis patients using blood ultrasound velocity and optical density dilution.", *ASAIO Journal* 2002 48(4), (Jul.-Aug. 2002),398-403.

Goovaerts, H. G., et al., "Microprocessor-based system for measurement of electrical impedances during haemodialysis and in postoperative care", *Medical & Biological Engineering & Computing*, vol. 26, (Jan. 1988),75-80.

Gotshall, R W., et al., "Bioelectric impedance as an index of thoracic fluid.", *Aviation Space and Environmental Medicine*, 70(1), (Jan. 1999),58-61.

Grimbert, F. , et al., "Pulmonary water and thoracic impedance. Evaluation of a measurement technic", *Annales de L'anesthésiologie Française*, 16 Spec No 2-3, French,(1975),157-63.

Harris, N. D., et al., "Applications of applied potential tomography (APT) in respiratory medicine", *Clinical Physics and Physiological Measurement*, 8 Suppl A, (1987),155-65.

Hatlestad, John D., et al., "Calibration of Impedance Monitoring of Respiratory Volumes Using Thoracic D.C. Impedance", U.S. Appl. No. 11/114,661, Date Mailed Apr. 26, 2005, 31 Pages.

Hatlestad, J. D., et al., "Physiological Response to Posture Change", U.S. Appl. No. 11/466,925, filed Aug. 24, 2006, 21 Pages.

Hoon, Raghunath S., et al., "Changes in Transthoracic electrical impedance at high altitude", *British Heart Journal*, vol. 39 (1977),61-66.

Hull, E. T., et al., "The Transthoracic Impedance Method for the Determination of the Degree and Change in Extravascular Water", *Acta Tuberc. Pneumol. Belg.*, 68(4), (1977),369-377.

Hull, E. T., et al., "Transthoracic electrical impedance: artifacts associated with electrode movement", *Resuscitation*, 6(2), (1978),115-124.

Ishibe, Y. , et al., "Transthoracic electrical impedance method for measurement of pulmonary edema in vivo", *Masui*; 27(13), Japanese,(Dec. 1978),1559-67.

Joekes, A. M., et al., "Impedance Cardiography—Its value in an intensive care unit", D) *Materiels et techniques/Cardiocirculatory Equipment and Technics*, Abstract No. 141, 1 Page.

Keller, Guido , et al., "Monitoring of Pulmonary Fluid Volume and Stroke Volume by Impedance Cardiography in Patients on Hemodialysis", *Chest*, 72(1), (Jul. 1977),56-62.

Khan, Mahfooz R., et al., "Quantitative electrical-impedance plethysmography for pulmonary oedema", *Medical & Biological Engineering & Computing*, (Nov. 1977),627-633.

Kiesler, T. W., et al., "Impedance cardiography by use of a spot-electrode array to track changes in cardiac output in anesthetized dogs.", *Journal of the American Veterinary Medical Association*, 196(11), (Jun. 1, 1990),1804-10.

Koizumi, T. , "Changes of transthoracic impedance (zinf 0 and deltaz) in newborn infants", *Acta Neonatol. Jpn.*, 14(3), (1978),335-340.

Kunst, P. W., et al., "Electrical impedance tomography in the assessment of extravascular lung water in noncardiogenic acute respiratory failure", *Chest*, 116(6), (Dec. 1999),1695-702.

Kusumoto, Fred M., et al., "Medical Progress: Cardiac Pacing", *New England Journal of Medicine*, 334(2), (Jan. 11, 1996),89-98.

Larsen, F. , et al., "Influence of furosemide and body posture on transthoracic electrical impedance in AMI", *Chest*, 90(5), (733-7),Nov. 1986.

Laszlo, Z. , et al., "Cardiovascular and Hormonal Changes with Different Angles of Head-up Tilt in Men", *Physiol. Res.*, vol. 50, (2001),71-82.

Lau, C P., et al., "Rate-responsive pacing with a pacemaker that detects respiratory rate (Biorate): clinical advantages and complications", *Clinical Cardiology*, 11(5), (May 1988),318-24.

Lau, C. P., "The range of sensors and algorithms used in rate adaptive cardiac pacing", *Pacing and clinical electrophysiology: PACE*, 15(8), (Aug. 1992),1177-211.

Leung, Zoe K., et al., "Feasibility of an automatic atrial and ventricular threshold determination using thransthoracic using impedance", *Pacing and Clinical Electrophysiology*, vol. 19, *Part II*, Abstract 263,(Apr. 1996),631.

Luepker, R. V., et al., "Transthoracic Electrical Impedance: Quantitative Evaluation of a Non-Invasive Measure of Thoracic Fluid Volume", *American Heart Journal*; 85(1), (Jan. 1973),83-93.

Mai, J. , et al., "Enhanced Rate Response Algorithm for Orthostatic Compensation Pacing", *Pacing Clin Electrophysiol*, 23, Naspe Abstracts, Abstract No. 678,(Apr. 2000),722.

McCarty, Richard N., et al., "Assessment of pulmonary edema in acute congestive heart failure with impedance cardiography", *J Am Osteopath Assoc.*, 74(9), (May 1975),879.

McNamee, James E., et al., "Peribronchial electrical admittance measures lung edema and congestion in the dog", *Special Communications, Electrical Admittance and Pulmonary Edema*, 377-341.

Newell, J. C., et al., "Assessment of ascute pulmonary edema in dogs by electrical impedance imaging", *IEEE Transactions on Biomedical Engineering*, 43(2), (Feb. 1996), 133-138.

Nierman, D. M., et al., "Evaluation of transthoracic bioelectrical impedance analysis in monitoring lung water during diuresis", *Applied Cardiopulmonary Pathophysiology*, 7(1), (1997),57-62.

Nierman, David M., "Transthoracic Bioimpedance Can Measure Extravascular Lung Water in Acute Lung Injury1", *Journal of Surgical Research* 65, Article No. 0350, (1996),101-108.

Noble, T. J., et al., "Diuretic induced change in lung water assessed by electrical impedance tomography", *Physiol Meas.*, 21(1), (Feb. 2000),155-63.

Nukiwa, Toshihiro , et al., "Responses of Serum and Lung Angiotensin-Converting Enzyme Activities in the Early Phase of Pulmonary Damage Induced by Oleic Acid in Dogs", *Am Rev Respir Dis.*, 126(6), (Dec. 1982),1080-1086.

Petersen, M E., et al., "Cardiac pacing for vasovagal syncope: a reasonable therapeutic option?", *Pacing Clin Electrophysiol.*, 20(3 Pt 2), (Mar. 1997),824-6.

Petersen, J. R., et al., "Electrical impedance measured changes in thoracic fluid content during thoracentesis", *Clin Physiol.*, 14(4), (Jul. 1994),459-66.

Platia, Edward V., et al., "Time Course of Transvenous Pacemaker Stimulation Impedance, Capture Threshold, and Electrogram Amplitude", *Pacing Clin Electrophysiol.*, 9(5), (Sep./Oct. 19),620-625.

Pomerantz, M , et al., "Transthoracic electrical impedance for the early detection of pulmonary edema", *Surgery*, 66(1), (Jul. 1969),260-8.

Raaijmakers, E. , et al., "Estimation of non-cardiogenic pulmonary oedema using dual-frequency electrical impedance.", *Medical & Biological Engineering & Computing*, 36(4), (Jul. 1998),461-6.

Raggueneau, J. L., et al., "Monitoring of intracellular and extracellular hydric compartments by body impedance", *Anesth Anal. Rean*, vol. 36, (1979),439-443.

Ramos, Marcos U., et al., "Transthoracic electric impedance. A clinical guide of pulmonary fluid accumulation in congestive heart failure", *Minnesota Medicine*, 58(9), (Sep. 1975),671-676.

Rosborough, John P., et al., "Electrical Therapy for Pulseless Electrical Activity", *NASPE*, 23(4), Part II, Abstract,(Apr. 2000),591.

Saunders, Charles E., "The Use of Transthoracic Electrical Bioimpedance in Assessing Thoracic Fluid Status in Emergency Department Patients", *American Journal of Emergency Medicine*, 6(4), (Jul. 1988),337-340.

Schuster, C. J., et al., "Application of Impedance Cardiography in Critical Care Medicine", *Resuscitation*, vol. 11, (1984),255-274.

Schwartzman, David , et al., "Serial Defibrillation Lead Impedance in Patients with Epicardial and Nonthoracotomy Lead System", *Journal of Cardiovascular Electrophysiology*, 7(8), (Aug. 1996),697-703.

Segev, G. , et al., "B-Type Natriuretic Peptide: A Novel Clinical Tool for Diagnosis and Management of Heart Failure", *Hospital Physician*, .,(Sep. 2003),19-24.

Shochat, M. , et al., "Internal thoracic impedance monitoring: a new prospect in acute heart failure", *European Heart Journal*, 25(*Supp*), (Aug.-Sep. 2004),p. 72-72.

Shoemaker, William C., et al., "Multicenter trial of a new thoracic electrical bioimpedance device for cardiac output estimation", *Critical Care Medicine*, 22(12), (Dec. 1994),1907-1912.

Smith, R. M., et al., "Canine thoracic electrical impedance with changes in pulmonary gas and blood volumes.", *Journal of Applied Physiology*, 53(6), (Dec. 1982),1608-13.

Spinale, F. G., et al., "Noninvasive estimation of extravascular lung water using bioimpedance.", *The Journal of Surgical Research*, 47(6), (Dec. 1989),535-40.

Spinelli, J. C., "Method and System for Treatment of Neurocardiogenic Syncore", U.S. Appl. No. 10/862,831, filed Jun. 7, 2004, 15 pages.

Sra, J S., et al., "Cardiac pacing during neurocardiogenic (vasovagal) syncope", *J Cardiovasc Electrophysiol.*, 6(9), (Sep. 1995),751-60.

Stadler, R. , et al., "Automated detection of decreases in intrathoracic impedance to predict CHF hospitalization", *Abstract* 263, 26(4 pt II), Abstract 16,(Apr. 2003),932.

Stahmann, Jeffrey , "Thoracic Impedance Detection With Blood Resistivity Compensation", U.S. Appl. No. 10/921,503, filed Aug. 19, 2004, 38 pgs.

Staub, N. C., "The measurement of lung water content.", *The Journal of Microwave Power*, 18(3), (Sep. 1983),259-63.

Tang, W., "Assessment of total body water using bioelectrical impedance analysis in neonates receiving intensive care", *Arch Dis Child Fetal Neonatal Ed.*, 77(2), (Sep. 1997),F123-6.

Tempel, G., et al., "Transthoracic electrical impedance in anaesthesia and intensive care.", *Resuscitation*, 6(2), (1978),97-105.

Thakur, Ranjan K., et al., "Pericardial Effusion Increases Defibrillation Energy Requirement", *Pacing Clin Electrophysiol.*, 16(6), (Jun. 1993),1227-1230.

Vainshtein, G. B., et al., "The Functioning of the Cerebral Circulation System in Hyperthermia in Rabbits", *Fiziol Zh SSSR Im I M Sechenova*, 75(11), (Nov. 1989),1608-1614.

Van De Water, Joseph M., et al., "Monitoring the Chest with Impedance", *Chest*, 64(5), (Nov. 1973),597-603.

Viirola, H, "Controlled growth of antimony-doped tin dioxide thin films by atomic layer epitaxy", *Thin Solid Films*, 251, (Nov. 1994),127-135.

Viirola, H, et al., "Controlled growth of tin dioxide thin films by atomic layer epitaxy", *Thin Solid Films*, 249(2) (Sep. 1994),144-149.

Visokay, M R., "Application of HfSiON as a gate dielectric material", *Applied Physics Letters*, 80(17), (Apr. 2002),3183-3185.

Wang, L., et al., "Impedance based prediction of CHF admission precedes symptoms in heart failure patients", *Heartrhythm : the official journal of the Heart Rhythm Society*, 1(Suppl 1), Abstract 679,(2004),S213.

Wang, Li, et al., "Multiple Sources of the Impedance Cardiogram Based on 3-D Finite Difference Human Thorax Models", *IEEE Transactions on Biomedical Engineering*, 42(2), (Feb. 1995),141-148.

Wang, L., et al., "Prediction of CHF hospitalization by ambulatory intrathoracic impedance measurement in CHF patients is feasible using pacemaker or ICD lead systems", *Pacing and Clinical Electrophysiology*, 26(4 pt. II), Abstract 123,(Apr. 2003),959.

Wuerz, Richard C., et al., "Effects of prehospital medications on mortality and length of stay in congestive heart failure", *Annals of Emergency Medicine*, 21(6), (Jun. 1992),669-74.

Yu, C., et al., "Changes in device based thoracic impedance in decompensating congestive heart failure", *Circulation*, 104(17 supplement),, Abstract 1994,(2001),II-419.

Yu, C. M., et al., "Correlation of device-based intra-thoracic impedance and patient fluid status during intravenous diuretic therapy in acute CHF", *European Heart Journal*, 23(Abstract Supplement).

Yu, C., et al., "Device-based intra-thoracic impedance correlates with fluid status and provides automaticed prediction of CHF hospitalization", *Journal of Cardiac Failure*, 10(4 Suppl), Abstract 354,(2004),S113.

Yu, Cheuk-Man, et al., "Early warning of CHF hospitalization by intra-thoracic impedance measurement in CHF patients with pacemakers", *Pacing and Clinical Electrophysiology*, 24, (Apr. 2001),19.

Yu, C., et al., "Early warning of CHF hospitalization by intrathoracic impedance measurement in CHF patients with pacemakers", *Pacing and Clinical Electrophysiology: PACE*, 24(4 pt II), Abstract 19,(2002),527.

Yu, C. M., et al., "Impedance measurements from implanted devices provide automated prediction of CHF hospitalization", *European Heart Journal*, 25(Supp), (Aug.-Sep. 2004)P27-27.

Yu, C. M., et al., "Intrathoracic impedance: A surrogate measure of fluid retention and predictor of hosptalization in patients with heart failure", *Journal of the American College of Cardiology*, 41(6 Supplement A), Abstract 1206-70,(2003),210A.

Zellner, J. L., et al., "Bioimpedance: a novel method for the determination of extravascular lung water.", *The Journal of Surgical Research*, 48(5), (May 1990),454-9.

Zima, E., "Intracardiac impedance in biventricular electrode configuration for left ventricular monitoring", *European Heart Journal*, 25(Supp), (Aug.-Sep. 2004),p. 165-165.

"U.S. Appl. No. 10/921,503, Supplemental Amendment and Response filed Oct. 25, 2007 to Office Action mailed Jul. 13, 2007", 24 pgs.

"U.S. Appl. No. 10/921,503, Non-Final Office Action mailed Jul. 13, 2007", 5 pgs.

"U.S. Appl. No. 11/132,109, Decision from Pre-Appeal Brief Review mailed Aug. 9, 2007", 2 pgs.

"U.S. Appl. No. 11/132,109, Final Office Action mailed Jan. 22, 2007", 13 pgs.

"U.S. Appl. No. 11/132,109, Non-Final Office Action Mailed Jul. 7, 2006", 10 pgs.

"U.S. Appl. No. 11/132,109, Notice of Allowance mailed Oct. 5, 2007", 10 pgs.

"U.S. Appl. No. 11/132,109, Pre-Appeal Brief Request for Review filed Apr. 23, 2007", 5 pgs.

"U.S. Appl. No. 11/132,109, Response filed Oct. 10, 2006 to Non-Final Office Action mailed Jul. 7, 2006", 20 pgs.

"U.S. Appl. No. 10/921,503, Response to Restriction Requirement and Preliminary Amendment filed Apr. 9, 2007", 19 pgs.

"U.S. Appl. No. 10/921,503, Restriction Requirement mailed Mar. 7, 2007", 6 pgs.

"U.S. Appl. No. 10/921,503, Notice of Allowance mailed Jan. 31, 2008", 8 pgs.

"U.S. Appl. No. 12/139,948, Non-Final Office Action mailed Feb. 6, 2009", 8 pgs.

"U.S. Appl. No. 12/139,948, Notice of Allowance mailed Sep. 4, 2009", 19 pgs.

"U.S. Appl. No. 12/139,948, Response filed Apr. 27, 2009 to Non Final Office Action mailed Feb. 6, 2009", 8 pgs.

"U.S. Appl. No. 12/628,384, Non-Final Office Action mailed Apr. 6, 2010", 5 Pgs.

"U.S. Appl. No. 12/628,384, Response filed Jul. 9, 2010 to Non Final Office Action mailed Apr. 6, 2010", 12 Pgs.

* cited by examiner

DETECTION OF PLEURAL EFFUSION USING TRANSTHORACIC IMPEDANCE

CROSS-REFERENCE TO RELATED APPLICATIONS

This application is a continuation of U.S. patent application Ser. No. 11/132,109, filed on May 18, 2005, which is now issued as U.S. Pat. No. 7,340,296, the specification of which is incorporated herein by reference in its entirety.

TECHNICAL FIELD

This patent document pertains generally to medical systems, devices, and methods, and more particularly, but not by way of limitation, to thoracic fluid detection.

BACKGROUND

Variations in how much fluid is present in a person's thorax can take various forms and can have different causes. For example, eating salty foods can result in retaining excessive fluid in the thorax, which is commonly referred to as "thoracic fluid," and elsewhere. Posture changes can also affect the amount of thoracic fluid present at a given time. For example, moving from a supine to standing position can shift intravascular fluid away from the thorax, toward the lower extremities.

Another cause of fluid build-up in a person's thorax is pulmonary edema, which involves buildup of extravascular fluid in the lungs. In pulmonary edema, fluid accumulates in extracellular spaces, such as the spaces between lung tissue cells. One cause of pulmonary edema is congestive heart failure (CHF), which is also sometimes referred to as "chronic heart failure" or simply as "heart failure." In many situations, CHF can be conceptualized as an enlarged weakened portion of heart muscle. The impaired heart muscle results in poor cardiac output of blood. As a result of the impaired heart muscle, fluid tends to pool in blood vessels in the lungs and becomes a barrier to normal oxygen exchange. This intravascular fluid buildup, in turn, results in the extravascular fluid buildup mentioned above. Accordingly, pulmonary edema may be an indicative and important condition associated with CHF.

Yet another example of thoracic fluid accumulation is pleural effusion, which is the buildup of extravascular fluid in the space between the lungs and the rib cage. The lungs are covered by a membrane called the pleura, which has two layers, an inner layer and an outer layer. The outer layer lines the rib cage and diaphragm. The inner layer covers the lungs. The pleura produces a fluid, which acts as a lubricant to help in breathing, allowing the lungs to move in and out smoothly. Pleural effusion is the accumulation of too much of such fluid. Pleural effusion, like pulmonary edema, may also result from CHF and provide an (early) indication that heart failure is present or has worsened.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

Figure 1:
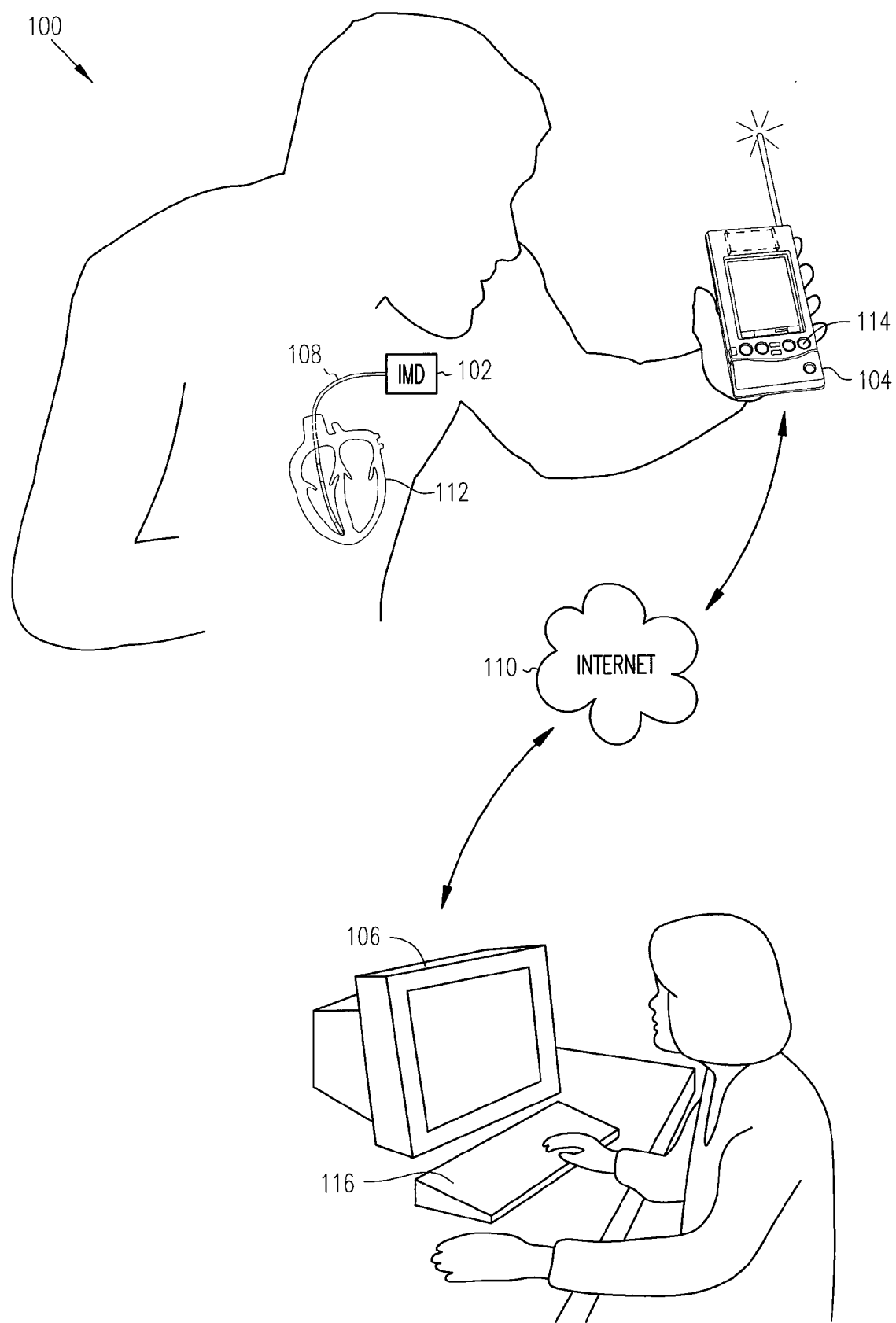
FIG. 1 is a schematic view illustrating a system comprising an implantable medical device (IMD) and one or more of external user interface communicable with the IMD, the system is adapted to detect the presence of thoracic fluid in a subject and determine the existence of one or both of: a pleural effusion indication and a pulmonary edema indication.

The following detailed description includes references to the accompanying drawings, which form a part of this detailed description. The drawings show, by way of illustration, specific embodiments in which the present systems, devices, and methods may be practiced. These embodiments, which are also referred to herein as "examples," are described in enough detail to enable those skilled in the art to practice the present systems, devices, and methods. The embodiments may be combined or varied, other embodiments may be utilized, or structural, logical or electrical changes may be made without departing from the scope of the present systems, devices, and methods. It is also to be understood that the various embodiments of the present systems, devices, and methods, although different, are not necessarily mutually exclusive. For example, a particular feature, structure or characteristic described in one embodiment may be included within other embodiments. The following detailed description is, therefore, not to be taken in a limiting sense, and the scope of the present systems, devices, and methods are defined by the appended claims and their equivalents.

In this document: the terms "a" or "an" are used to include one or more than one; the term "or" is used to refer to a nonexclusive or, unless otherwise indicated; the terms "near-DC thoracic impedance signal(s)" (or simply "near-DC component") are defined to include thoracic impedance signals at frequencies less than the frequencies at which cardiac stroke and respiration components (of thoracic impedance signals) lie, which is typically understood to include signal frequencies from 0 Hz to about 0.05 Hz, inclusive (e.g., cardiac stroke and respiration components of thoracic impedance signals lie at frequencies greater than 0.05 Hz); the term "intravascular" includes the term "intracardiac"; the term "thorax" refers to a human subject's body between the neck and diaphragm; the term "subject" is used synonymously with the term "patient"; the term "user" includes a caregiver, a subject, a loved one or others who may ascertain or provide physiologic information, patient symptom information, or posture information to the present systems, devices, and methods; the term "treatment" includes, among other things, a therapy directed to an underlying cause of a thoracic fluid build-up or the thoracic fluid build-up itself; the meaning of the term "detect" includes "determining the existence of"; and the meaning of the phrase "significant thoracic impedance signal" includes a thoracic impedance signal numerically less than, or substantially equal to, a thoracic impedance threshold value.

Furthermore, all publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

Introduction

Today, heart failure is a major cause of hospital admissions in the United States as it contributes to more than 4 million hospitalizations per year. According to recent statistics, hospitalizations for heart failure cost upwards of 12 billion dollars per year. Many of these hospital admissions are due to (excessive) fluid accumulation in the thorax of subjects, which is challenging to treat and often goes undetected until such subjects are critically ill. It is estimated that in the United States, pleural effusion affects 1.3 million people each year.

Morbidity and mortality of heart failure can potentially be lowered with accurate detection and appropriate treatment of the disease in its early stages. As mentioned above, both pleural effusion and pulmonary edema may provide an (early) indication of heart failure. Thus, the detection of pleural effusion or pulmonary edema may reduce or eliminate the need for subjects with heart failure to require hospital admission. A reduction or elimination of the need for hospitalization results in lower health care costs.

EXAMPLES

Detection of both pleural effusion and pulmonary edema may be made by monitoring an impedance of a subject's thoracic cavity. In each case, a reduction in thoracic impedance indicates the presence of an increase in thoracic fluid. Conversely, fluid depletion in the thorax corresponds to an increase in the thoracic impedance detected. In pleural effusion, a reduction in thoracic impedance indicates an increase in the amount of fluid between the pleural membranes outside the subject's lungs. In pulmonary edema, a reduction in thoracic impedance indicates an increase in the amount of fluid inside the subject's lungs. Since reduced thoracic impedance will occur with either of pleural effusion and pulmonary edema, differential detection of these conditions may be useful. One example of such usefulness arises from the fact that treatment requirements (e.g., therapy) may differ depending on whether pleural effusion or pulmonary edema or both are responsible for a reduction in thoracic impedance sensed.

The present systems, devices, and methods may differentiate pleural effusion and pulmonary edema using, in addition to sensed thoracic impedance, one or a combination of: physiological information, patient symptom information, and posture information. The present inventors have recognized that while some patient symptoms (e.g., dyspnea) may be associated with both pleural effusion and pulmonary edema, other patient symptoms (e.g., a pleuritic chest pain or one or more hiccups) are unique to pleural effusion. The present inventors have also recognized that sensed thoracic impedance may change at a greater rate with a change in posture orientation when pleural effusion is present than when pulmonary edema is present. Further, the present inventors have recognized that physiologic information (e.g., one or more respiratory sounds) may also be useful in differentiating pleural effusion and pulmonary edema.

The present systems, devices, and methods may also advantageously improve a "sensitivity" or a "specificity" of thoracic fluid detection using, at least in part, the physiologic information, the patient symptom information, or the posture information. Sensitivity generally refers to the ability of a detection scheme to effectively detect that which a user desires to detect or treat. Specificity generally refers to the ability of a detection scheme to avoid erroneous or "false" detections of that which a user desires to detect or treat. The desire for an effective detection system generally involves a tradeoff between sensitivity and specificity, both of which must be simultaneously adequate to ensure acceptable detection system performance. As discussed below, when the physiologic information, the patient symptom information, or the posture information point toward the presence of thoracic fluid, a base thoracic impedance threshold is adjusted (improving sensitivity or specificity) to account for such information.

The techniques for detecting thoracic fluid and differentiating between pleural effusion and pulmonary edema, as described herein, may be implemented in an IMD adapted to perform detection and differentiation only or in an IMD configured to also deliver a therapy. In one example, the IMD is a cardiac rhythm management (CRM) device adapted to provide bradycardia pacing therapy, cardioversion/defibrillation therapy, drug therapy, or cardiac resynchronization therapy. Such therapy may be particularly useful since heart failure subjects with pleural effusion or pulmonary edema may also benefit from, for example, resynchronization pacing which can improve cardiac function by causing the ventricles of a subject's heart to contract in a more coordinated manner. Examples of resynchronization devices are described in Kramer, et al., U.S. Pat. No. 6,574,506, entitled "SYSTEM AND METHOD FOR TIMING SYNCHRONIZED PACING," assigned to Cardiac Pacemakers, Inc., and hereby incorporated by reference in its entirety.

This patent document discusses, among other things, systems, devices, and methods that will be described in applications involving IMDs including, but not limited to, implantable CRM systems such as pacemakers, cardioverter/defibrillators, pacer/defibrillators, biventricular or other multi-site resynchronization or coordination devices, and drug delivery systems. However, the systems, devices, and methods described herein may also be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing detection, differentiation, or therapy.

FIG. 1 is a schematic view illustrating generally, by way of example, a system 100 capable of detecting the presence of thoracic fluid and determining the existence of one or a combination of: a pleural effusion indication and a pulmonary edema indication using, in addition to sensed thoracic impedance, physiologic information, patient symptom information, or posture information. In this example, the system 100 includes an implantable medical device (IMD) 102, such as a cardiac rhythm management (CRM) device, and one or more external user interfaces 104, 106. IMD 102 may be a battery-powered device that is implanted subcutaneously in a subject's chest or elsewhere and connected to electrodes associated with the subject's heart 112 by one or more leadwires 108. In this example, at least one external user interface 104 or 106 is configured to wirelessly communicate with IMD 102. As an example, IMD 102 may communicate with external user interface 104 or other device (which is typically nearby), or with external user interface 106 or other device (which is typically distant), via Internet 110 or other communication modality.

Figure 3:
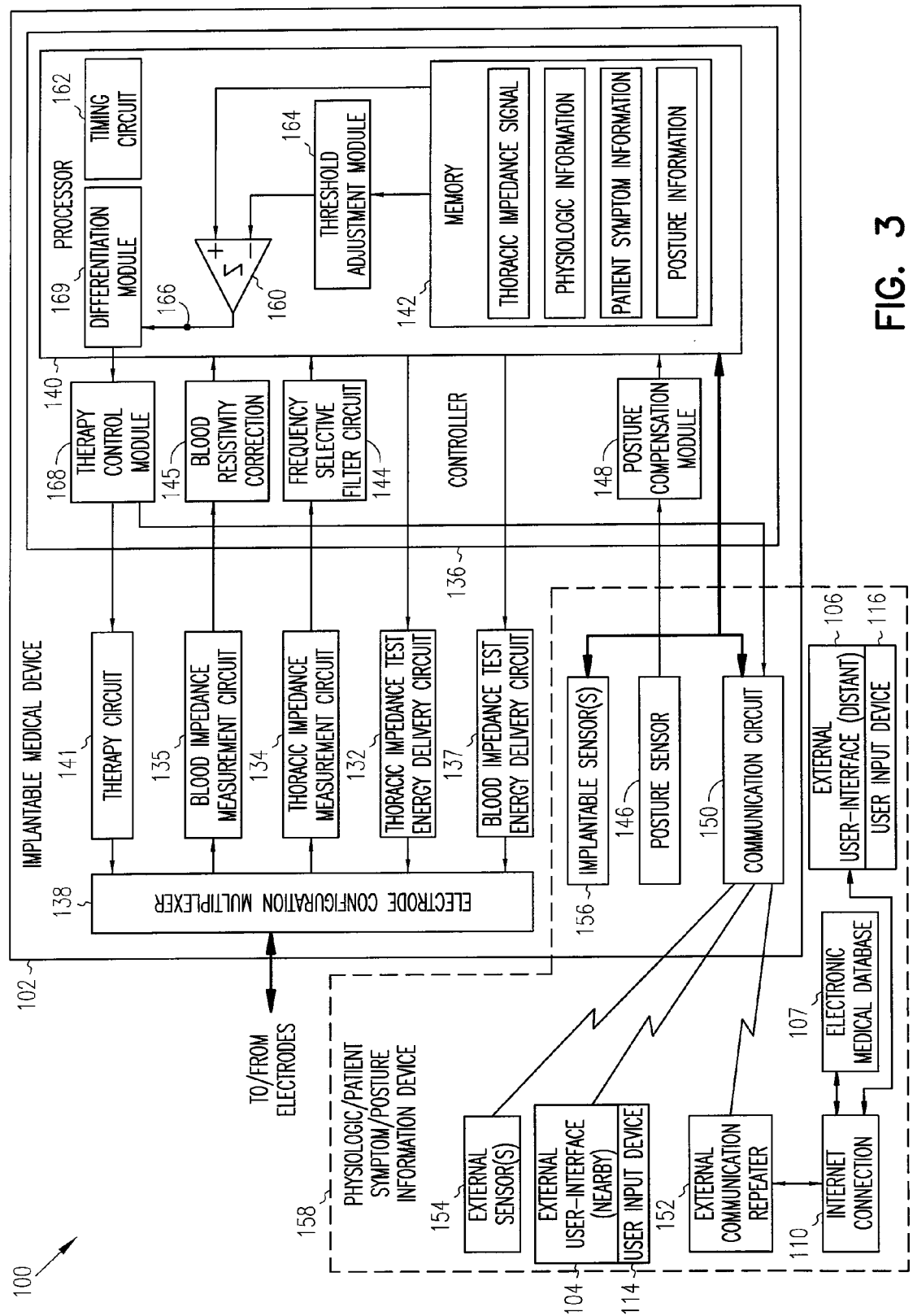
FIG. 3 is a schematic diagram illustrating a portion of a system adapted to detect the presence of thoracic fluid in a subject and determine the existence of one or a combination of: a pleural effusion indication and a pulmonary edema indication.

In varying examples, at least one external user interface 104 or 106 includes a user input device 114 or 116, respectively. Each user input device 114 or 116 may be configured to collect physiologic information (e.g., a deemed indication of one or more respiratory sounds), patient symptom information (e.g., a deemed presence or severity of pleuritic chest pain or a deemed intensity or frequency of one or more hiccups), or posture information (e.g., an indication of a supine or standing position) from a user. In one example, the user input device 114 or 116 functions as a physiologic information device into which the user can enter physiologic information about the subject. In another example, the user input device 114 or 116 functions as a patient symptom device into which the user can enter patient symptom information about the subject. In yet another example, the user input device 114 or 116 functions as a posture information device into which the user can enter posture information (such as a thoracic orientation from a predetermined reference) of the subject. In varying examples, each user input device 114 or 116 is adapted to transmit the physiologic information, the patient symptom information or the posture information to a processor 140 (FIG. 3).

Figure 2:
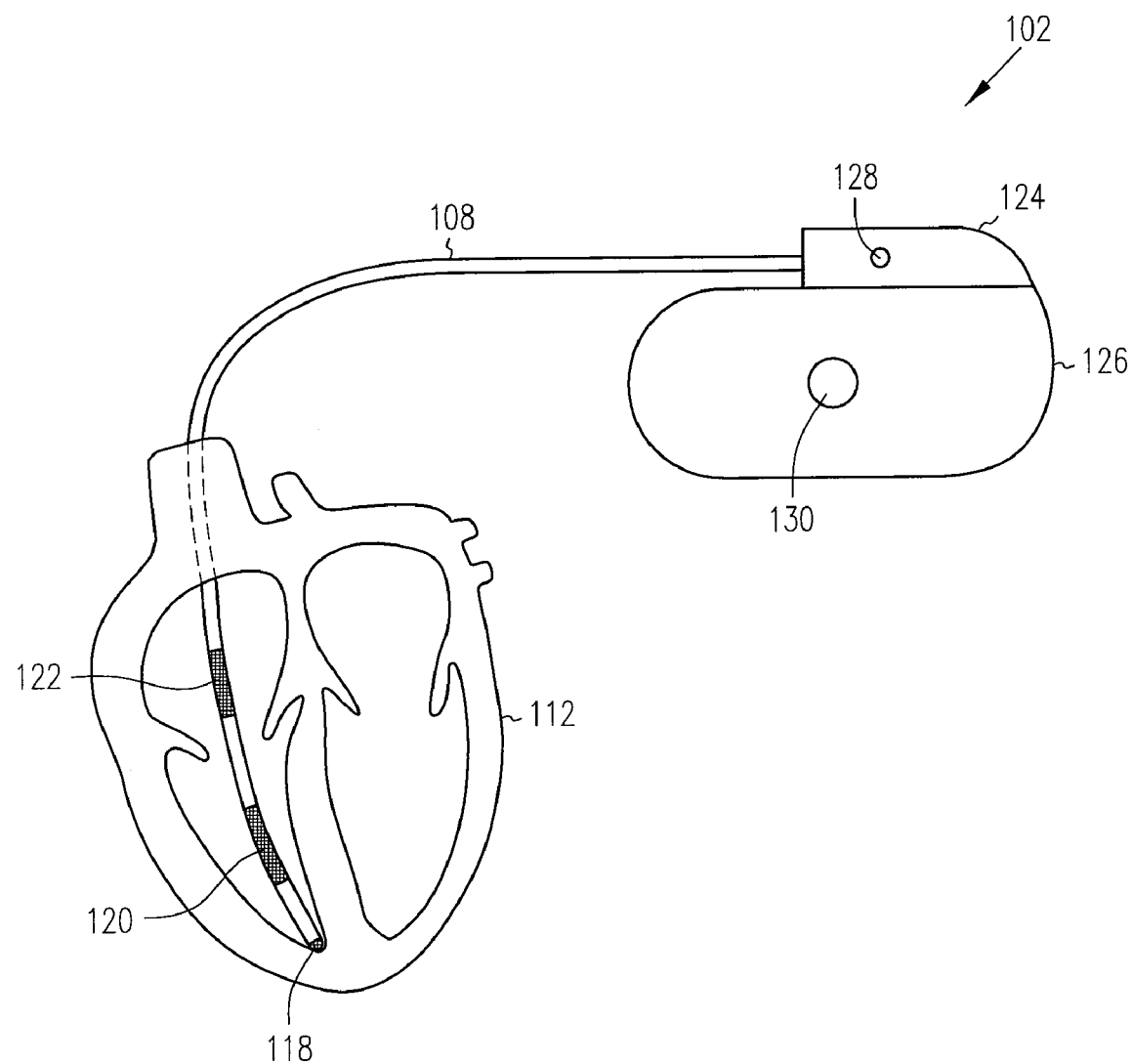
FIG. 2 is a schematic view illustrating an IMD for use in a system adapted to detect the presence of thoracic fluid in a subject and determine the existence of one or a combination of: a pleural effusion indication and a pulmonary edema indication.

FIG. 2 is a schematic view illustrating generally, by way of example, an IMD 102 suitable for use in a system 100 capable of detecting the presence of thoracic fluid and determining the presence of one or a combination of: a pleural effusion indication and a pulmonary edema indication. The exemplary IMD 102 of FIG. 2 is adapted to sense a thoracic impedance of a subject, which as discussed above, provides an indication of the fluid amount within the subject's thorax. In this example, IMD 102 is coupled to the heart 112 using one or more leadwires 108, such as a multi-electrode leadwire. In this example, leadwire 108 includes a tip electrode 118, a distal ring electrode 120, and a proximal ring electrode 122, each of which is disposed in the right side of heart 112. In this example, each of the tip electrode 118, the distal ring electrode 120, and the proximal ring electrode 122 is independently electrically connected to a separate corresponding electrically conductive terminal within an insulating header 124. The header 124 is affixed to a hermetically sealed housing 126, which may be formed from a conductive metal, such as titanium. In this example, the housing 126 carries various electronic components of IMD 102. The housing 126 may additionally house or communicate with at least one implantable device. The housing 126 may be substantially covered over its surface by a suitable insulator, such as silicone rubber. In this example, the header 124 includes a header electrode 128, and the housing 126 includes a housing electrode 130.

In one example, a thoracic impedance measurement circuit senses a thoracic impedance signal by delivering a test current between: (1) at least one of the ring electrodes 120 or 122, and (2) the housing electrode 130; and a resulting responsive voltage is measured across the tip electrode 118 and the header electrode 128. When IMD 102 is implanted at some distance away from the heart 112 (e.g., pectorally), this electrode configuration injects the test current over a substantial portion (but possibly not the entire portion) of the subject's thorax, such that when the resulting voltage measurement is divided by the test current magnitude, it yields an indication of thoracic impedance. Using different electrodes for delivering the current and for measuring the responsive voltage reduces the component of the measured impedance signal that results from ohmic losses at the tissue-sense electrode interface and in the leadwires to the test current delivery electrodes.

While such a "four-point" probe (probe using four electrodes) is useful, it is not required. In other examples, a "three-point" probe (probe using three electrodes, with one electrode used for both test current delivery and responsive voltage measurement), or a "two-point" probe (probe using two electrodes, each electrode used for both test current delivery and responsive voltage measurement) are used. Moreover, other electrode configurations could alternatively be used to implement a four-point probe. The above described four-point provides one example of a suitable four-point probe configuration. Other illustrative examples of four-point probe circuits for sensing thoracic impedance signals from a subject, are described in Hauck et al., U.S. Pat. No. 5,284,136 entitled, "DUAL INDIFFERENT ELECTRODE PACEMAKER," which is assigned to Cardiac Pacemakers, Inc., and herein incorporated by reference in its entirety, including its description of performing thoracic impedance measurements.

FIG. 3 is a schematic diagram illustrating generally, by way of example, portions of a system 100 capable of detecting the presence of thoracic fluid and determining the existence of one or a combination of: a pleural effusion indication and a pulmonary edema indication. FIG. 3 illustrates one conceptualization of various modules, devices, and circuits, which are implemented either in hardware or as one or more sequences of steps carried out on a microprocessor or other controller. Such modules, devices, and circuits are illustrated separately for conceptual clarity; however, it is to be understood that the various modules, devices, and circuits of FIG. 3 need not be separately embodied, but may be combined or otherwise implemented, such as in software or firmware.

In one example, the system 100 differentiates pleural effusion and pulmonary edema using, in addition to sensed thoracic impedance, physiologic information (e.g., a deemed indication of one or more respiratory sounds), patient symptoms (e.g., a deemed presence or severity of pleuritic chest pain or a deemed intensity or frequency of one or more hiccups), or posture information (e.g., a subject's thoracic orientation). Using the physiologic information, the patient symptom information, or the posture information, the system 100 may also adjust a detection threshold of thoracic fluid detection (thereby adjusting a sensitivity or specificity of system 100). The detection threshold refers to the threshold of a detection scheme at which the condition(s) a user desires to detect or treat is declared to be present. In this example, the system 100 includes a hermetically sealed IMD 102 and at least one programmer or other external user interface 104 or 106. In varying examples, the at least one external user interface 104 or 106 includes a user input device 114 or 116, as discussed above. In this example, an intracardiac leadwire 108 connects IMD 102 with a subject's heart 112.

The example of FIG. 3 includes a thoracic impedance test energy delivery circuit 132 that, together with a thoracic impedance measurement circuit 134, senses a thoracic impedance signal from the subject. In accordance with instructions provided by a controller 136, an electrode configuration multiplexer 138 couples the thoracic impedance test energy delivery circuit 132 and the thoracic impedance measurement circuit 134 to one or more appropriate electrodes associated with the subject's thorax. By way of such electrodes, the thoracic impedance measurement circuit 134 may accurately sense a thoracic impedance signal from the subject. In this example, the multiplexer 138 is coupled to a therapy circuit 141, such as a pulse delivery circuit, for delivering therapy (e.g., pacing, resynchronization, ATP, cardioversion, or defibrillation) by way of one or more electrodes 118, 120, or 122. In one example, therapy is provided to the subject in response to instructions provided by the controller 136 and received by the therapy circuit 141. In another example, a timing circuit 162 is used in the delivery of the therapy to the subject.

Other illustrative examples of electrode configurations and circuits for sensing thoracic impedance signals from a subject, are described in Hartley et al., U.S. Pat. No. 6,076,015 entitled, "RATE ADAPTIVE CARDIAC RHYTHM MANAGEMENT DEVICE USING TRANSTHORACIC IMPEDANCE," which is assigned to Cardiac Pacemakers, Inc., and herein incorporated by reference in its entirety, including its description of performing thoracic impedance measurements. The Hartley et al., U.S. Pat. No. 6,076,015, uses thoracic impedance signals to obtain respiration signals. In contrast, the present systems, devices, and methods described herein use thoracic impedance signals to obtain an indication of a fluid amount within the subject's thorax; however, both thoracic fluid amount and respiration signals are obtainable using the thoracic impedance measurement techniques described in Hartley et al. In one example of the present systems, devices, and methods, the thoracic fluid amount is obtained from a lower frequency (e.g., a "near-DC" (less than 0.05 Hz)) portion of the thoracic impedance signal rather than the frequencies of the respiration signal described in Hartley et al.

In this document, the near-DC component of the thoracic impedance signal refers to the frequencies below which respiration and cardiac contractions significantly influence the thoracic impedance signal (e.g., at least a factor of two lower than the respiration component). In one example, the near-DC component of the thoracic impedance signal refers to signal frequencies below a cutoff frequency having a value of about 0.05 Hz, such as at signal frequencies from 0 Hz to about 0.05 Hz (inclusive), because the cardiac stroke and respiration components of the thoracic impedance signal lie at higher frequencies. Noteworthy is that near-DC frequencies include DC frequency.

In varying examples of the system 100, the controller 136 may include a processor 140 or any other means capable of sequencing through various control states and having executable instructions stored in an associated memory storage device, a microsequencer, or a state machine. In the illustrative example of FIG. 3, the controller 136 includes a processor 140. In one example, the processor 140 performs any filtering or other signal processing needed to extract the near-DC component from the sensed thoracic impedance signal by processing a stored sequence of executable instructions. In this example, the filtering or signal processing is performed by dedicated filtering hardware (e.g., a frequency selective filter circuit 144 coupled to the processor 140). In yet another example, the filtering or signal processing is performed in an external device such as an external user interface 104 or 106. Although the processor 140 is illustrated as being integrated within the IMD 102 in FIG. 3, the processor 140 or other sequencing means may also be located external to the IMD 102, such as being integrated with one or more external user interface 104 or 106.

As discussed above, variations in how much fluid is present in a subject's thorax can take various forms and can have different causes. Beyond pleural effusion, pulmonary edema, and eating salty foods for example, posture changes may also affect an amount of fluid the subject has in their thorax. As an example, moving from a supine to a standing position can shift intravascular fluid away from the subject's thorax toward the subject's lower extremities thereby decreasing the amount of thoracic fluid present. For this reason, the system 100 of FIG. 3 includes a posture sensor 146 adapted to sense the subject's posture orientation. In one example, the posture sensor 146 senses a "posture signal" which is indicative of the subject's then-current posture. A different posture signal is provided for different postures (e.g., a posture signal for upright postures differs from a posture signal for recumbent postures). One example of a suitable posture sensor 146 commercially available is a two-axis accelerometer, such as Model No. ADXL202E, manufactured by Analog Devices, Inc. of Norwood, Mass., USA; however, other posture sensors may also be used without departing from the scope of the present systems, devices, and methods.

In this example, the posture signal sensed by the posture sensor 146 is used to remove a posture component from the sensed thoracic impedance signal resulting in a "posture-compensated" thoracic impedance signal. In one example, a posture compensation module 148 may be used to remove the posture component using the posture signal corresponding to the then-current posture sensed by the posture sensor 146. For example, the posture compensation module 148 may numerically increase a sensed thoracic impedance signal value when the posture sensor 146 senses the subject's then-current posture as being supine. The rationale being that the subject's supine orientation may have affected the amount of fluid in the subject's thorax and thus, the sensed thoracic impedance signal value. The timing circuit 162 may be used to assign each sensed thoracic impedance signal to the then-current posture signal. For instance, in this example the timing circuit 162 is used in conjunction with memory 142 to store a thoracic impedance signal sensed at time 1 with a posture signal sensed at time 1, a thoracic impedance signal sensed at time 2 with a posture signal sensed at time 2, . . . , a thoracic impedance signal sensed at time N with a posture signal sensed at time N.

The thoracic impedance signal sensed may also be affected by confounding factors other than the amount of fluid present in the thorax. One such confounding factor is any change in blood resistivity. Blood resistivity changes as a function of hematocrit in the blood. The hematocrit (Ht) or packed cell volume (PCV) is the proportion of blood that is occupied by red blood cells. It is typically between 0.35 and 0.52, and is slightly higher, on average, in males than in females. For example, when the subject is dehydrated, there will be less fluid in the subject's blood. Therefore, the subject's hematocrit level will increase, that is, the subject's blood will include a higher percentage of other components, such as insulative red blood cells. This will increase the blood resistivity, which, in turn may affect the sensed thoracic impedance signal even though it is not necessarily associated with the extravascular fluid accumulation of pleural effusion or pulmonary edema. Other factors that are believed to possibly influence blood resistivity include the subject's electrolyte level, certain medications in the blood, proteins in the blood, or blood gas concentrations.

As an illustrative example, the above change in hematocrit percentage from 35% to 52% may correspond to a change in resistivity from about 140 $\Omega \cdot cm$ to about 200 $\Omega \cdot cm$. Such changes in blood resistivity may influence the sensed thoracic impedance. This may confound thoracic fluid amount determination using the sensed thoracic impedance, unless the extravascular thoracic fluid amount determination is corrected for such variations in blood resistivity, if any.

Accordingly, the system in FIG. 3 illustrates a blood impedance measurement circuit 135. The blood impedance measurement circuit 135 receives a blood impedance measurement from electrodes that are associated with blood (and preferably blood in the thorax) such as in response to a delivery of test energy by a blood impedance test energy delivery circuit 137. In one example, the blood impedance measurement circuit 135 and the blood impedance test energy delivery circuit 137 are configured similar to the thoracic impedance measurement circuit 134 and the thoracic impedance test energy delivery circuit 132, respectively, as discussed above, except for being connected to different electrodes. Using the blood impedance measurement, the controller 136 executes a sequence of instructions to compute a blood resistivity correction 145. In this example, the blood resistivity correction 145 is applied to the sensed thoracic impedance signal that is received by the processor 140. This yields a "blood resistivity-compensated" thoracic impedance signal.

In FIG. 3, the thoracic impedance test energy delivery circuit 132 is illustrated separately from the blood impedance test energy delivery circuit 137 to assist the reader's conceptualization. In practice, these circuits, or portions thereof, may be combined. The combined circuit may be coupled to different electrodes for delivering the thoracic impedance test energy than for delivering the blood impedance test energy. Similarly, in FIG. 3, the thoracic impedance measurement circuit 134 is illustrated separately from the blood impedance measurement circuit 135 to assist the reader's conceptualization. In practice, these circuits, or portions thereof, may be combined. The combined circuit may be coupled to different electrodes for measuring the responsive voltages for the thoracic and blood impedance measurements. Illustrative examples of performing such thoracic and blood impedance measurements are described in Stahmann et al., U.S. patent application Ser. No. 10/921,503, entitled "THORACIC IMPEDANCE DETECTION WITH BLOOD RESISTIVITY COMPENSATION," which is assigned to Cardiac Pacemakers, Inc., and herein incorporated by reference in its entirety.

Once established, the sensed thoracic impedance signal or variation thereof (e.g., near-DC thoracic impedance signal, posture-compensated thoracic impedance signal, or blood resistivity-compensated thoracic impedance signal) may be compared to a thoracic impedance threshold value to determine whether such thoracic impedance signal is "significant." In the example of FIG. 3, a comparator 160 compares the sensed thoracic impedance signal or variation thereof to a thoracic impedance threshold. A significant thoracic impedance signal is a signal indicative of the presence of thoracic fluid. In this example, as discussed above, a reduction in a thoracic impedance signal indicates the presence of an increase in thoracic fluid. It follows that a significant thoracic impedance signal is a signal whose value is numerically less than, or substantially equal to, a thoracic impedance threshold value.

In one example, the thoracic impedance threshold is a base thoracic impedance threshold value. The base thoracic impedance threshold value is a thoracic impedance boundary established to differentiate between thoracic impedance signals that are significant (e.g., indicative of the presence of excessive thoracic fluid) and impedance signals that are nonsignificant (e.g., not indicative of the presence of excessive thoracic fluid). As an example, a thoracic impedance signal or variation thereof that is numerically less than, or substantially equal to, the base thoracic impedance threshold indicates the presence of excessive thoracic fluid. Conversely, a thoracic impedance signal that is numerically greater than the base thoracic impedance threshold indicates that no excessive thoracic fluid amount is present and the process repeats (e.g., a thoracic impedance signal is sensed and again compared to the base thoracic impedance threshold). In this example, the base thoracic impedance threshold is subject-specific (e.g., individualized to the patient) and determined by a caregiver, such as at the time of implantation. In another example, the base thoracic impedance threshold is nonsubject-specific (e.g., a standardized threshold). In this example, the base thoracic impedance threshold is programmed into system the 100, such as the processor 140.

In another example, the thoracic impedance threshold is an adjusted thoracic impedance threshold value which represents a change in a sensitivity or specificity to the detection of the presence of thoracic fluid over the base thoracic impedance threshold. The adjusted thoracic impedance threshold value is generated from the base thoracic impedance threshold in addition to information collected or sensed by a physiologic/patient symptom/posture information device 158. As an example, information collected or sensed by device 158 that is indicative of the presence of (excessive) thoracic fluid results in the adjusted thoracic impedance threshold being numerically increased from the base thoracic impedance value. In a similar manner, but numerically opposite, information received or sensed by device 158 that points away from the presence of (excessive) thoracic fluid decreases (or leaves unchanged) the thoracic impedance threshold from the base thoracic impedance value. In this example, a threshold adjustment module 164 computes the adjusted thoracic impedance threshold value using the information collected or sensed by device 158.

In another example, although not illustrated, the sensed thoracic impedance signal or variation thereof is changed using the information collected or sensed by physiologic/patient symptom/posture information device 158. As an example, information received or sensed by device 158 that points toward the presence of (excessive) thoracic fluid decreases the sensed thoracic impedance signal value. Conversely, information received or sensed by device 158 that points away from the presence of (excessive) thoracic fluid increases (or leaves unchanged) the sensed thoracic impedance signal value.

Comparing the sensed thoracic impedance signal or variation thereof to the base or adjusted thoracic impedance threshold value provides an indication of whether thoracic fluid present in the subject is significant and thus requiring attention. In the example of FIG. 3, a binary indication at node 166 controls a therapy control module 168 that responsively adjusts or initiates a therapy to the subject, such as cardiac rhythm management therapy or drug therapy (e.g., diuretic). In one example, the therapy control module 168 is integrated within IMD 102. In another example, the therapy control module 168 is located externally to IMD 102, such as integrated with an external user-interface 104 or 106. In this example, the binary indication at node 166 is provided to a communication circuit 150, which is capable of communicating to the subject or other user, via external user interface 104 or 106, information about whether any significant thoracic fluid amount is present.

In this example, the system 100 includes the physiologic/patient symptom/posture information device 158 to collect information for use in differentiating pleural effusion and pulmonary edema or to increase a sensitivity or specificity of thoracic fluid detection. If, and when, a significant thoracic impedance is recognized, the processor 140 executes instructions to detect one or both of: a pleural effusion indication and a pulmonary edema indication using the information acquired by the device 158. In the example of FIG. 3, the physiologic/patient symptom/posture device 158 includes one or a combination of: an external sensor 154, an external user interface 104 (which is typically nearby) including user input device 114, an external communication repeater 152, an Internet connection 110, an electronic medical database 107, an external user interface 106 including user input device 116 (which is typically distant), one or more implantable sensors 156 including the posture sensor 146, and a communication circuit 150.

The physiologic/patient symptom/posture information device 158 shown is adapted to collect information from a user or sense information internally via sensor 156 or externally via sensor 154 and provide such information to the IMD 102. In one example, input device 158 is a physiologic information device to collect physiologic information about the subject and provide such information to system 100. The physiologic information collected by the system 100 may include a dullness or flatness of at least one respiratory sound. In another example, device 158 is a patient symptom information device to collect patient symptom information about the subject and provide such information to system 100. As an example, the patient symptom information collected may include the presence, absence, or severity of a pleuritic chest pain or the presence, absence, or intensity of one or more hiccups. In yet another example, device 158 is a posture information device to receive posture information of the subject and provide such information to system 100. As an example, the posture information collected by the system 100 may include a posture orientation relative to a predetermined posture reference (e.g., number of degrees the subject's thoracic cavity is inclined form a horizontal reference).

In the example of FIG. 3, the IMD 102 carries various electrical components, such as the communication circuit 150, which is capable of wirelessly communicating with a communication circuit of the external user interface 104. In another example, the communication circuit 150 wirelessly communicates with a communication circuit of (distant) external user interface 106 by way of nearby communication repeater 152. In this example, the repeater 152 is coupled to the external user interface 106 by way of Internet connection 110. Also in this example, the communication circuit 150 of IMD 102 is communicatively coupled to a communication circuit of the external sensor 154. The IMD 102 may additionally or alternatively include the implantable sensor 156 therewithin or implanted nearby and coupled thereto.

In varying examples, the system 100 includes at least one memory 142 that is capable of storing information collected or sensed by device 158 (e.g., physiologic information, patient symptom information, posture signal(s)), the thoracic impedance measurement circuit 134, or the blood impedance measurement circuit 135. In the example of FIG. 3, the memory 142 is capable of storing one or a combination of: a sensed thoracic impedance signal, a near-DC thoracic impedance signal, a posture-compensated thoracic impedance signal, a blood resistivity-compensated thoracic impedance signal, physiologic information, patient symptom information, and posture information. In this example, the memory 142 is also adapted to store weights (e.g., Weight 1, Weight 2, . . . , Weight N). Each weight corresponds to a type of information collected by device 158, such as a pitch of a respiratory sound, a presence of pleuritic chest pain, a severity of pleuritic chest pain, a presence of one or more hiccups, an intensity of one or more hiccups, a frequency of one or more hiccups, or a change in thoracic impedance with a change in posture orientation relative to a reference. Each weight may be numerically different, such as the numerically greatest weight may correspond to a type of information collected by device 158 which points towards a greatest likelihood of (e.g., having the strongest correlation with) a pleural effusion indication. In a similar manner, the numerically lowest weight may correspond to a type of information collected which points towards the least likelihood of (e.g., having the weakest correlation with) a pleural effusion indication. In another example, one or more of the weights are used in one or more algorithms to differentiate pleural effusion and pulmonary edema or to increase a sensitivity or specificity of the presence of thoracic fluid detection. In yet another example, the weights are obtained from historical information of one or more subjects previously found to have experienced pleural effusion. In such an example, the historical information is stored in the electronic medical database 107 coupled to Internet connection 110.

In the example of FIG. 3, a differentiation module 169 is adapted to differentiate pleural effusion and pulmonary edema. Such differentiation may use one or a combination of: the physiologic information, the patient symptom information, and the posture information. In one example, the differentiation module 169 weights (e.g., Weight 1, Weight 2, . . . , Weight N) one or more of: the physiologic information, the patient symptom information, and the posture information when differentiating pleural effusion and pulmonary edema.

Figure 4:
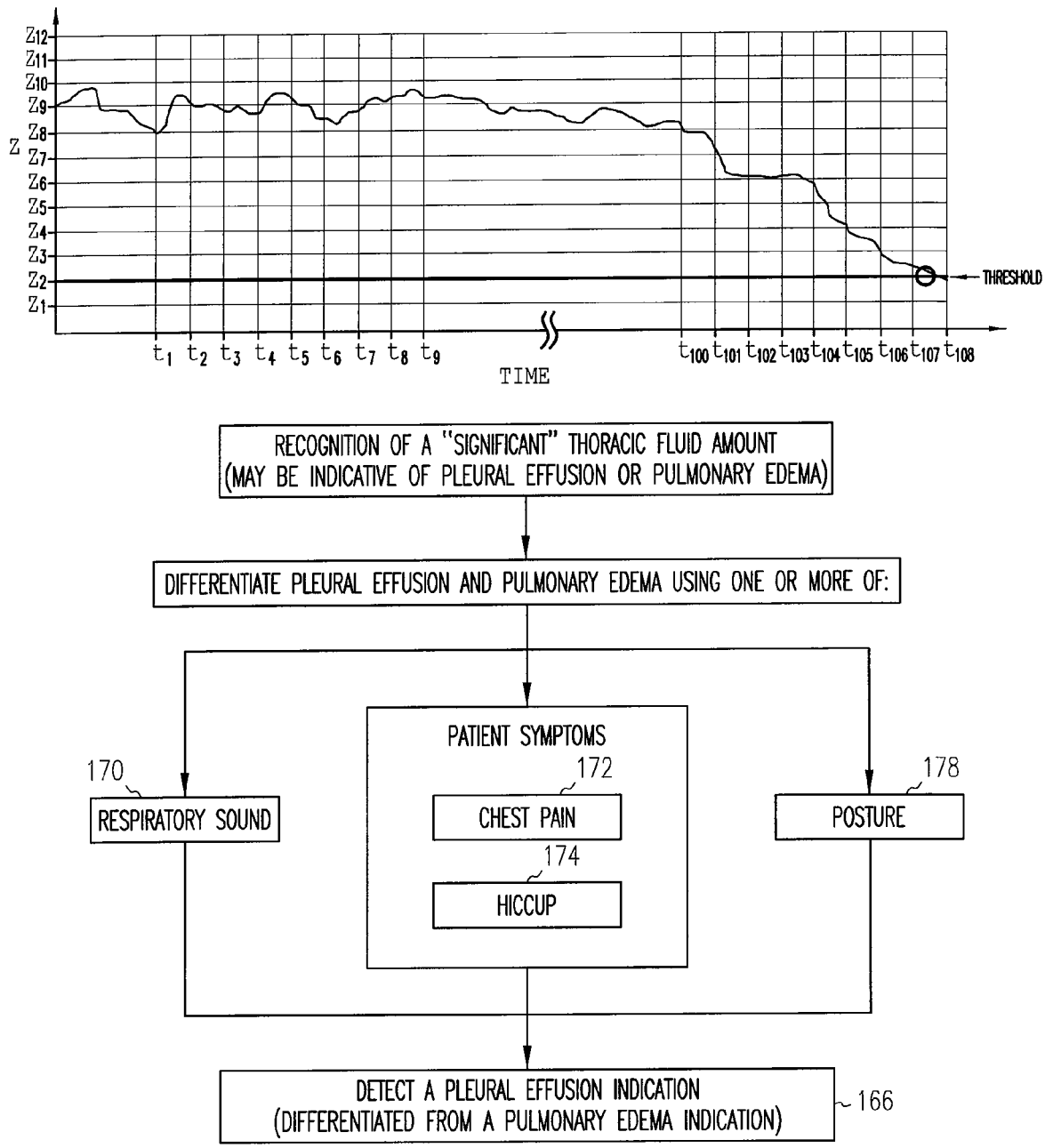
FIG. 4 is a flow chart including exemplary factors which may be used to differentiate a pleural effusion indication and a pulmonary edema indication.

FIG. 4 is a flow chart including factors for differentiating pleural effusion and pulmonary edema once a significant thoracic impedance is recognized (e.g., a thoracic impedance signal value less than, or substantially equal to, a thoracic impedance threshold value). In the example of FIG. 4, a thoracic impedance signal (Z) is shown that generally decreases as time (t) increases. As discussed above, this indicates the amount of thoracic fluid present in a subject is increasing. The thoracic impedance signal crosses a thoracic impedance threshold value between $t_{107}$ and $t_{108}$. In this example, the crossing of the thoracic impedance threshold denotes that a significant amount of fluid is present in the subject's thorax, which may be the result of one or both of: pleural effusion and pulmonary edema.

The present systems, devices, and methods allow physiologic information, patient symptom information, and posture information to be collected or sensed and processed to differentiate pleural effusion and pulmonary edema. As an example, the present systems, devices, and methods use one or a combination of: at least one respiratory sound 170 (physiologic information), a pleuritic chest pain 172 (patient symptom information), one or more hiccups 174 (patient symptom information), and a rate of change in thoracic impedance with a change in posture 178 (posture information) to differentiate pleural effusion from pulmonary edema.

In one example, a subject's respiratory sound 170 is used to differentiate pleural effusion and pulmonary edema. In one example, the at least one respiratory sound 170 is measured by an implantable sensor 156, which includes a microphone, accelerometer, or other like sound detector. In another example, a caregiver listens to the sound of the subject's breathing with a stethoscope (or other external sound detector) and may further tap on the subject's chest to listen for dullness. This act or technique is sometimes simply referred to as "percussion." When listening to the subject's breathing and tapping on the subject's chest, the caregiver typically does so in a symmetrical manner (e.g., first listens to the left side, then listens to the right side in approximately the same location to determine if any difference in sound exists). Whether the at least one respiratory sound 170 is sensed by implantable sensor 156 or detected by a caregiver, an indication of the sound ascertained is communicated to the processor 140. In the latter case, the indication is entered into external user interface 104 or 106 of the physiologic/patient symptom/posture device 158. A flat or dull sound resulting from the percussion points toward a pleural effusion detection; while, a wheeze or sharp sound is typically associated with pulmonary edema. In one example, a pleural effusion detection is differentiated from a pulmonary edema detection using, at least in part, one or more respiratory sound.

In another example, a subject's pleuritic chest pain 172 is used to differentiate pleural effusion and pulmonary edema. In one example, the subject enters an indication of an intensity of the pleuritic chest pain (e.g., a number on a scale of 1-10, with "10" being greatest pain) into external user interface 104 or 106. In another example, the caregiver examines the subject, such as by performing a lung scan, an x-ray of the subject's chest, or questioning of the subject, and thereafter enters a deemed indication of the pleuritic chest pain into external user interface 104 or 106. Although there are many possible underlying causes and intensities of pleuritic chest pain, which may not be the result of pleural effusion (e.g., underlying cause may be other problems associated with the heart, lungs, esophagus, muscles, ribs, tendons, or nerves), pleuritic chest pain in conjunction with a significant thoracic impedance signal correlates to an indication of pleural effusion. On the other hand, pleuritic chest pain 172 is typically not associated with pulmonary edema. One rationale for the association between pleuritic chest pain and pleural effusion is that the abnormal buildup of fluid around the lungs (which is present in pleural effusion) may press on the lungs, making it difficult for the subject's lungs to fully expand. In some situations, part or all of the lung will collapse. This collapse often causes pleuritic chest pain. The pleuritic chest pain is historically described by subjects as sharp or stabbing and is exacerbated with deep inhalation. In one example, pleural effusion is differentiated from pulmonary edema using, at least in part, any presence of pleuritic chest pain.

In another example, a subject's hiccups 174 are used to differentiate between pleural effusion and pulmonary edema. In one example, a user enters an indication of the presence, intensity, frequency, or duration of one or more hiccups (e.g., a number on a scale of 1-10, with "10" being one or a combination of: high presence, intensity, frequency, and duration of the hiccups) into external user interface 104 or 106. In another example, the caregiver examines the subject, such as by questioning the subject regarding the one or more hiccups in detail and enters a deemed indication of the severity of the subject's hiccups into external user interface 104 or 106. As an example, the caregiver may ask the subject questions regarding the time pattern of the hiccups, such as: (1) Do you get hiccups easily?, or (2) How long has the current episode of hiccups lasted? In another example, the caregiver may ask the subject questions regarding possible aggravating factors of the hiccups, such as: (1) Have you recently consumed something that was either hot or spicy? (hot and spicy foods or liquids may be a cause of hiccups), (2) Have you recently consumed carbonated beverages? (carbonation may be a cause of hiccups), or (3) Have you recently been exposed to any fumes? (noxious fumes may be a cause of hiccups). In another example, the caregiver may ask the subject questions regarding relieving factors, such as: (1) What have you done to try to relieve the hiccups?, (2) What has been effective for you in the past?, (3) How effective was the attempt at home treatment (e.g., holding breath, breathing repeatedly into a paper bag, drinking a glass of cold water, or eating a teaspoon of sugar)?, or (4) Did the hiccups stop for a while and then restart? In another example, the caregiver may ask the subject, or examine the subject, to determine what other symptoms are present in addition to hiccups 174. In yet another example, the one or more hiccups are measured by an implantable sensor 156, which includes a microphone, accelerometer, or other sound or vibration detector and automatically communicated to the processor 140.

A hiccup is a sound produced by an unintentional movement of the muscle at the base of the lungs, a location also commonly referred to as the "diaphragm," followed by rapid closure of the vocal chords. Although hiccups may be caused by noxious fumes, hot and spicy foods or liquids, tumor(s) affecting the "hiccup center" in the brain, or abdominal surgery; hiccups in conjunction with a significant thoracic impedance signal, points towards an indication of pleural effusion. On the other hand, hiccups are typically not associated with pulmonary edema. One rationale for the association between hiccups and pleural effusion is that hiccups may be the result of an irritation of the nerves that control the diaphragm. Such irritation may be due to lung inflammation. The normally smooth pleural surfaces, which are now roughened by the inflammation, rub together with each breath. As a result, fluid may accumulate at the site of the pleural inflammation. As mentioned above, pleural effusion is the abnormal fluid accumulation outside of the lungs. In one example, pleural effusion is differentiated from pulmonary edema using, at least in part, the presence of one or more hiccups.

In another example, a subject's rate of change in thoracic fluid with a change in posture orientation is used to differentiate pleural effusion and pulmonary edema. In one example, the subject's posture 178 is measured by a posture sensor 146. In another example, an indication of the subject's posture 178 is entered into external user interface 104 or 106 by a user. As an example, the indication of the subject's posture 178 is an inclination amount (e.g., approximate degree incline) from a reference (e.g., horizontal reference). Thoracic fluid outside of the lungs (associated with pleural effusion) shifts faster than fluid inside of the lungs (associated with pulmonary edema) when posture changes. Thus, when a rapid change in impedance occurs with a change in posture, such rapid change points toward an indication of pleural effusion and away from an indication of pulmonary edema.

FIG. 4 combines a significant thoracic fluid detection (e.g., thoracic impedance signal value less than, or substantially equal to, a thoracic impedance threshold value) with one or a combination of: at least one respiratory sound 170, a pleuritic chest pain 172, one or more hiccups 174, and a thoracic impedance change with a change in posture 178 to detect a pleural effusion indication 166. The above discussed differentiation factors 170-178 are not meant to be exhaustive, and may include other physiological information, other patient symptoms, or other posture information to differentiate pleural effusion and pulmonary edema.

An IMD's detection scheme is typically characterized by its "sensitivity" and "specificity." As discussed above, sensitivity generally refers to the ability of the detection scheme to effectively detect that which the caregiver desires the IMD to detect or treat; while specificity generally refers to the ability of the detection scheme to avoid improperly detecting or treating that which the caregiver determines that the device should not treat. Ideally, an IMD would have both 100% sensitivity and 100% specificity. However, for practical IMDs, there exists a tradeoff between sensitivity and specificity.

Figure 5:
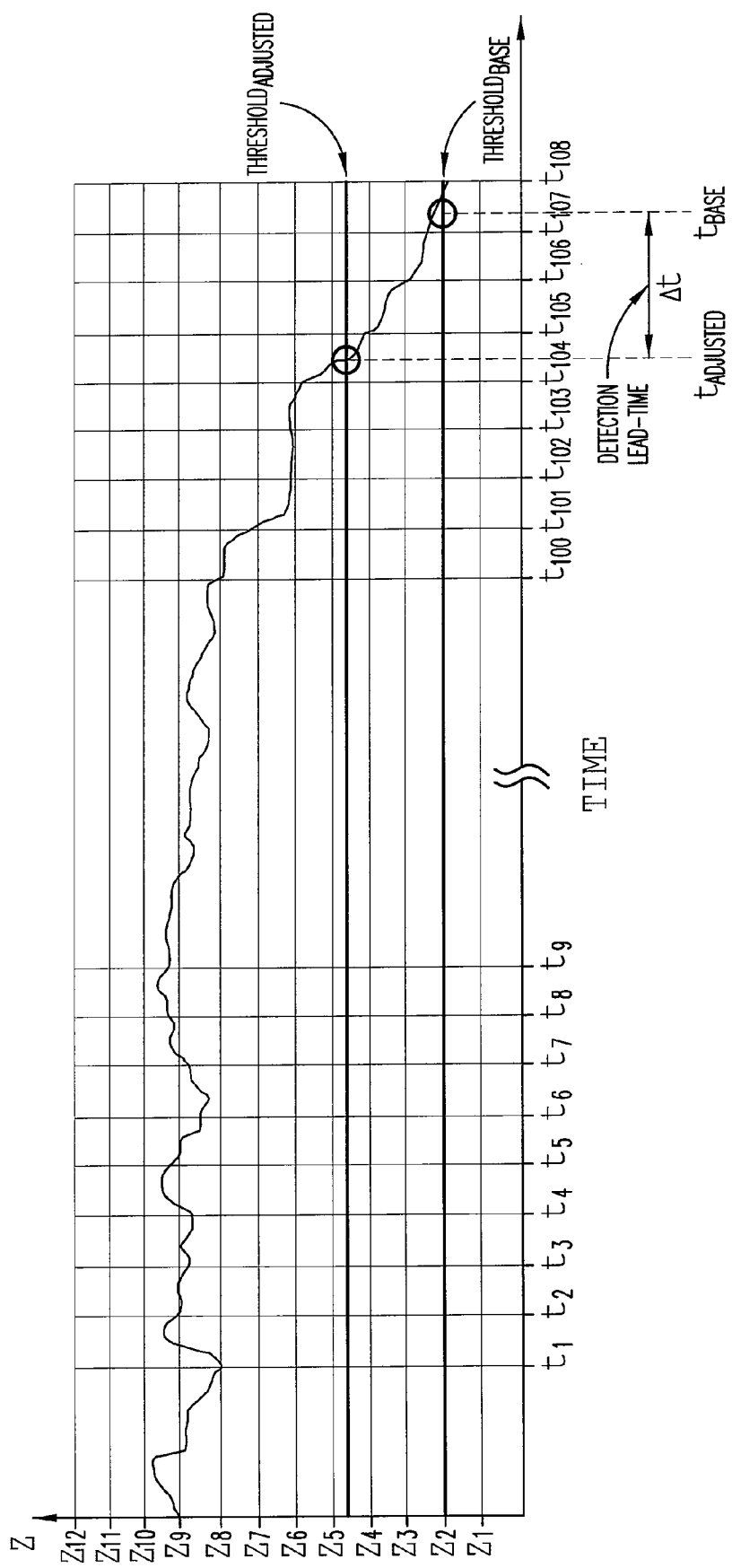
FIG. 5 is a graph illustrating an increase in sensitivity of thoracic fluid detection performed by the present systems, devices, and methods.

As discussed above, early detection of the presence of thoracic fluid may reduce or eliminate the need for hospital admission of a subject with heart failure. Therefore, it may be desirable to increase sensitivity of thoracic fluid detection beyond what can be obtained from a device that merely senses thoracic impedance. For a given detection system, this results in reduced specificity due to the tradeoff between sensitivity and specificity (discussed above). If specificity is reduced too much, the detector may give many spurious detections resulting in the user no longer trusting in its accuracy. Therefore, the present systems, devices, and methods are intended to provide increased sensitivity of thoracic fluid detection for a given level of specificity, as illustrated in FIG. 5. Alternatively, the present systems, devices, and methods may be used to provide improved specificity for a given level of sensitivity, or some combined simultaneous improvement of both sensitivity and specificity.

FIG. 5 is a graph illustrating an increase in sensitivity of the present systems, devices, and methods which detect the presence of thoracic fluid in a subject. The increase in sensitivity of detection may provide a detection lead time and thus, alert a user of a significant thoracic fluid amount sooner than a lower sensitivity system would provide. As discussed above, as fluid accumulation in the thorax of a subject increases, thoracic impedance decreases. Conversely, as fluid in the thorax depletes, thoracic impedance increases. Typically, a thoracic impedance signal includes cardiac stroke, respiration, posture, or blood resistivity components. Thus, in some examples, the thoracic impedance signal used in comparison to a thoracic impedance threshold is obtained by filtering or compensating the thoracic impedance signal to obtain a near-DC, posture-compensated, or blood resistivity-compensated thoracic impedance signal, respectively. In this example, a near-DC component of the thoracic impedance signal refers to signal frequencies below a cutoff frequency having a value of about 0.05 Hz, such as at signal frequencies from 0 Hz to about 0.05 Hz, because the cardiac stroke and respiration components of the thoracic impedance signal lie at higher frequencies (e.g., >about 0.05 Hz). In another example, a posture compensation module 148 compensates the thoracic impedance signal using, in part, a posture signal provided by a posture sensor 146. In yet another example, the thoracic impedance signal is adjusted to compensate for changes in blood resistivity. In the illustrative example of FIG. 5, a near-DC thoracic impedance signal is graphed versus time.

In one example, the system 100 recognizes a significant thoracic fluid amount by comparing the near-DC thoracic impedance signal value to a base thoracic impedance threshold value. If, and when, the near-DC thoracic impedance signal value is less than, or substantially equal to, the base thoracic impedance threshold value, the subject, caregiver, or other user is alerted that a significant thoracic fluid amount is present; thus, indicating the possible presence of one or both of: pleural effusion and pulmonary edema. In the example of FIG. 5, the near-DC thoracic impedance signal (Z) crosses the base thoracic impedance threshold (Threshold$_{Base}$) at time t$_{Base}$.

The system 100 enhances the detection of thoracic fluid using, in addition to the sensed, filtered, or compensated thoracic impedance, information collected or sensed by physiologic/patient symptom/posture information device 158 to adjust the base thoracic impedance threshold, resulting in Threshold$_{Adjusted}$. In one example, information collected or sensed by device 158 that is indicative of the presence of thoracic fluid results in the adjusted thoracic impedance threshold value being numerically increased from the base thoracic impedance value. In a similar manner, but numerically opposite, information collected or sensed by device 158 that points away from the presence of thoracic fluid decreases (or leaves unchanged) the thoracic impedance threshold from the base thoracic impedance value. As an example, suppose device 158 collects or senses information from the subject including: flat or dull respiratory sounds, an indication of high intensity pleuritic chest pain, an indication of a high frequency of hiccups, and a large rate of change in thoracic impedance with a change in posture. As discussed above, such information is indicative of the presence of thoracic fluid (specifically, points toward the presence of pleural effusion). Accordingly, a numerically increased threshold from Threshold$_{Base}$ to Threshold$_{Adjusted}$ results. In the example of FIG. 5, the near-DC thoracic impedance signal (Z) crosses a Threshold$_{Adjusted}$ at time t$_{Adjusted}$, resulting in a timely alert to the subject or caregiver. As shown, Threshold$_{Adjusted}$ results in an earlier (by Δt) alert compared to Threshold$_{Base}$. Although the foregoing example included the comparison of a near-DC thoracic impedance signal to a base or adjusted thoracic impedance threshold, the present systems, devices, and methods are not so limited. The use of a non-filtered, non-compensated (e.g., sensed) thoracic impedance signal, a posture-compensated thoracic impedance signal, or a blood resistivity-compensated thoracic impedance signal is also within the scope of the present systems, devices, and methods.

Figure 6:
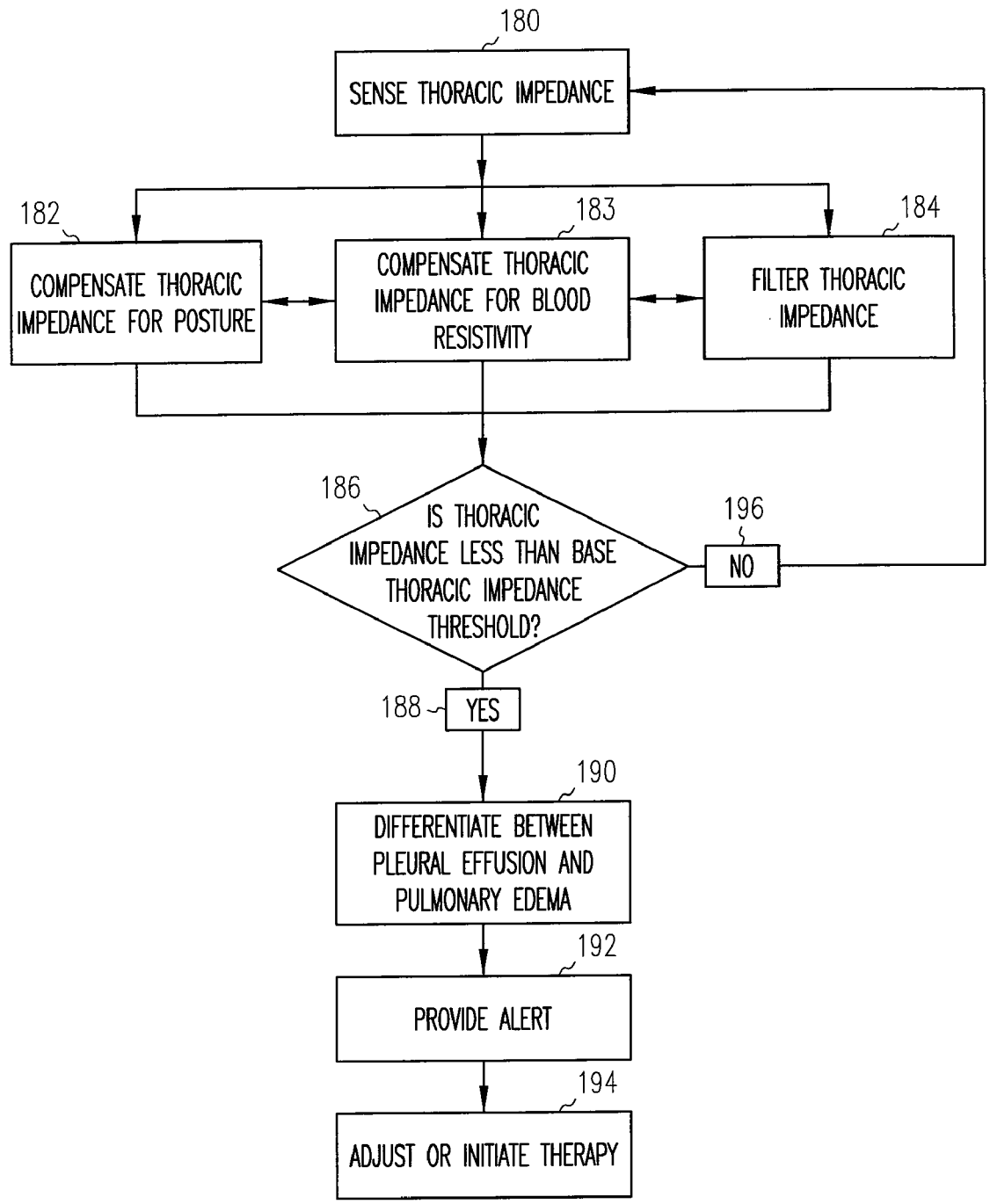
FIG. 6 is a flow chart illustrating one method of detecting the presence of thoracic fluid in a subject and determining the existence of one or a combination of: a pleural effusion indication and a pulmonary edema indication.

FIG. 6 is a flow chart illustrating one method of detecting the presence of thoracic fluid in a subject and determining the presence of one or both of: pleural effusion and pulmonary edema. The present method senses the presence of thoracic fluid and determines the cause of such thoracic fluid accumulation (e.g., pleural effusion or pulmonary edema). At 180, a thoracic impedance signal is sensed. This may be accomplished in a number of ways. In one example, a thoracic impedance signal is measured by delivering a test current between: (1) at least one ring electrode 120 or 122; and (2) a housing electrode 130, and a resulting responsive voltage is measured across a tip electrode 118 and a header electrode 128. In another example, the delivering the test current includes injecting a four-phase carrier signal, such as between the housing electrode 130 and one of the ring electrodes 120 or 122. In one such example, the first and third phases use +320 microampere pulses that are 20 microseconds long. The second and fourth phases use −320 microampere pulses that are also 20 microseconds long. The four phases are repeated at 50 millisecond intervals to provide a test current signal from which a responsive voltage may be measured.

At 182, the sensed thoracic impedance signal or variation thereof (e.g., near-DC thoracic impedance signal or blood resistivity-compensated thoracic impedance signal) is compensated for posture. There are a number of ways in which this can be accomplished. In one example, the system 100 includes a posture sensor 146 and a posture compensation module 148. The posture sensor 146 provides a posture signal indicating a subject's then-current posture. The posture compensation module 148 compensates the sensed thoracic impedance signal using the posture signal. For instance, if a posture signal indicates a subject is in a supine orientation, the posture compensation module 148 may increase the sensed thoracic impedance signal since the supine orientation may have decreased the thoracic impedance signal sensed (indicating an increase in thoracic fluid), as discussed above.

At 183, the sensed thoracic impedance signal or variation thereof (e.g., posture-compensated thoracic impedance signal or near-DC thoracic impedance signal) is compensated for blood resistivity. There are a number of ways in which this can be accomplished. In one example, the blood impedance measurement is performed in the same manner as the thoracic impedance measurement (discussed above), except that measurement of the responsive voltage is across two electrodes that are both typically located in the same chamber of the subject's heart 112 or same blood vessel. Once measured, the controller 136, using the blood impedance measurement, executes a sequence of instructions to compute a blood resistivity correction 145. This blood resistivity correction 145 can then be applied to the sensed thoracic impedance or variation thereof that is received by processor 140. Illustrative examples of compensating the thoracic fluid indication for blood resistivity are described in Stahmann et al., U.S. patent application Ser. No. 10/921,503, entitled "THORACIC IMPEDANCE DETECTION WITH BLOOD RESISTIVITY COMPENSATION," which is assigned to Cardiac Pacemakers, Inc., and herein incorporated by reference in its entirety, including its equations for representing the blood resistivity-compensated thoracic impedance signal. In one example, the sensed thoracic impedance signal is compensated for blood resistivity at 183 before being compensated for posture at 182.

At 184, the sensed thoracic impedance signal or variation thereof (e.g., posture-compensated thoracic impedance signal or blood resistivity-compensated thoracic impedance signal) is filtered. This results in a near-DC thoracic impedance signal. The filtering may be accomplished in a number of ways. In one example, a processor 140 of the system 100 performs any filtering or other signal processing needed to extract from the thoracic impedance signal a near-DC component. In another example, a frequency selective filter circuit 144 performs any filtering or other signal processing needed to extract from the thoracic impedance signal a near-DC component. In another example, the sensed thoracic impedance signal is filtered at 184 to obtain a near-DC thoracic impedance signal before being compensated for posture at 182. In yet another example, the sensed thoracic impedance signal is filtered at 184 to obtain a near-DC thoracic impedance signal before being compensated for blood resistivity at 183.

At 186, the near-DC thoracic impedance signal, the posture-compensated thoracic impedance signal, or the blood resistivity-compensated thoracic impedance signal is compared to a base thoracic impedance threshold value. As discussed above, the base thoracic impedance threshold value defines a boundary between a significant thoracic fluid amount and an insignificant thoracic fluid amount. In one example, the comparison includes determining whether the near-DC thoracic impedance signal is less than, or substantially equal to, the base thoracic impedance threshold value. Where the near-DC thoracic impedance is greater than the base thoracic impedance threshold value, a non-significant indication of thoracic fluid results at 196 and process flow returns to 180. In examples where the near-DC thoracic impedance is less than, or substantially equal to, the thoracic impedance threshold, a significant indication of abnormal thoracic fluid accumulation results at 188. Although the foregoing included the comparison of a near-DC thoracic impedance signal to a base thoracic impedance threshold, the present systems, devices, and methods are not so limited. The use of a non-filtered, non-compensated (e.g., sensed) thoracic impedance signal, posture-compensated thoracic impedance signal, or blood resistivity-compensated thoracic impedance signal is also within the scope of the present systems, devices, and methods.

At 190, the system 100 determines whether the significant thoracic fluid amount was caused by pleural effusion or pulmonary edema or both. In one example, pleural effusion is differentiated from pulmonary edema using one or a combination of: at least one respiratory sound 170, a pleuritic chest pain 172, one or more hiccups 174, and a rate of change in thoracic impedance with a change in posture 178. At 192, the system timely alerts the subject or the caregiver to an indication of pleural effusion or pulmonary edema. The alert may be provided in a number of ways. In one example, an audible tone is sounded, which prompts the subject to call his/her caregiver. If the subject is linked to a remote monitoring system (e.g., via a communication repeater 152), the alert can be electronically communicated to the caregiver. In another example, the alert may be provided (e.g., displayed) to the subject or caregiver at the subject's next visit to his/her caregiver. In one example, at 194, a therapy is adjusted or initiated in response to the detection of one or both of: pleural effusion or pulmonary edema at 190. As an example, the therapy is selected from a group consisting of: cardiac rhythm management therapy or drug therapy. Notably, the therapy provided to the subject may differ depending on whether pleural effusion or pulmonary edema or both are detected.

Figure 7:
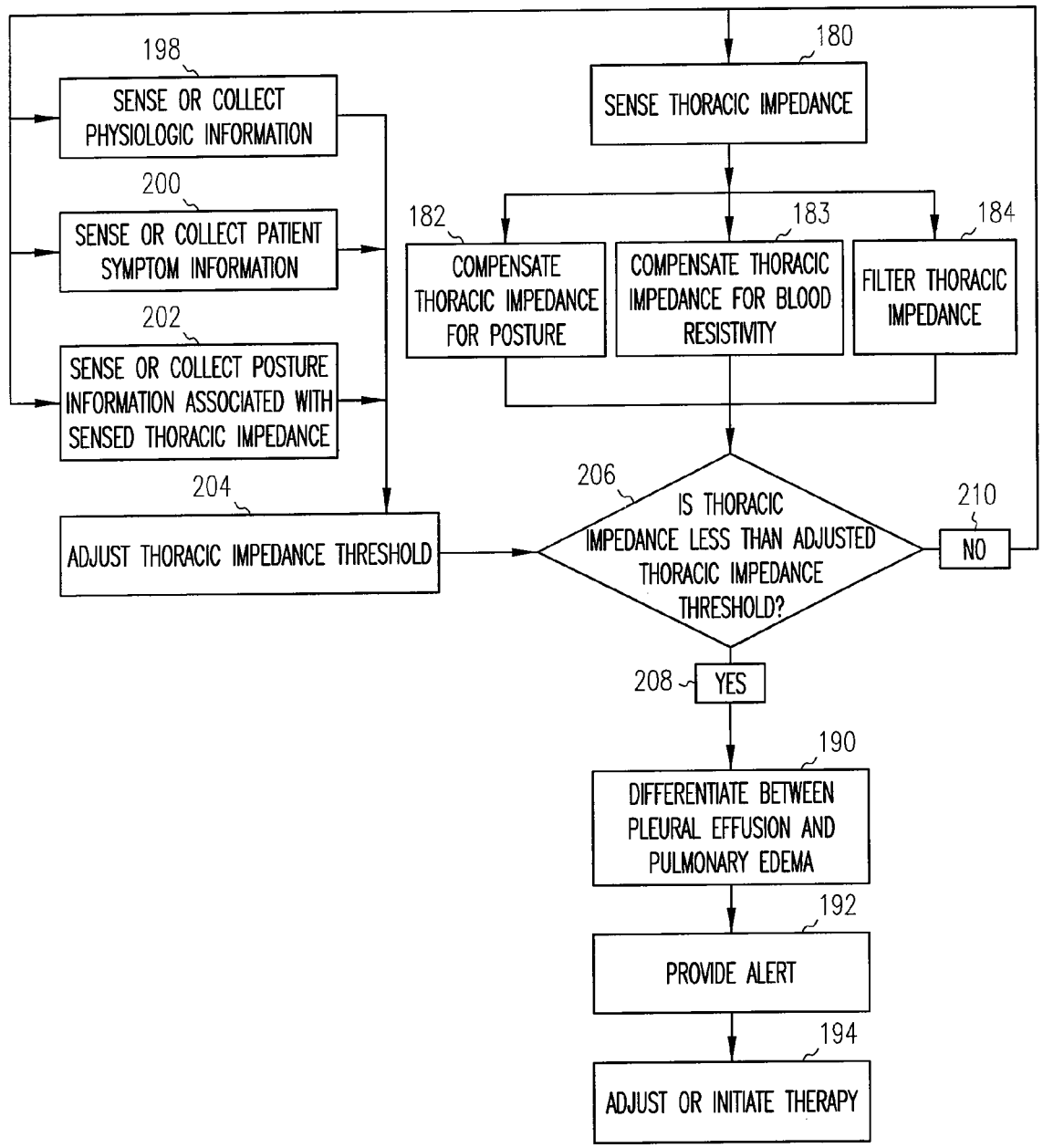
FIG. 7 is a flow chart illustrating one method of increasing a sensitivity of thoracic fluid detection in a subject and detecting one or a combination of: a pleural effusion indication and a pulmonary edema indication.

FIG. 7 is a flow chart illustrating one method of increasing the sensitivity of the presence of thoracic fluid detection in a subject and determining the existence of one or a combination of: pleural effusion and pulmonary edema. At 180, a thoracic impedance signal is sensed, such as discussed above. At 182, the sensed thoracic impedance signal or variation thereof is compensated for posture, as also discussed above. At 183, the sensed thoracic impedance signal or variation thereof is compensated for blood resistivity, as also discussed above. At 184, the sensed thoracic impedance signal or variation thereof is filtered to obtain a near-DC thoracic impedance signal, as further discussed above.

At 198, physiologic information is sensed or collected. There are a number of ways in which the physiologic information may be sensed or collected. In one example, the physiologic information sensed or collected includes at least one respiratory sound 170. As an example, the at least one respiratory sound 170 is measured by an implantable sensor 156, which includes a microphone, accelerometer, or other like sound detector. In another example, a caregiver listens to the sound of the subject's breathing with a stethoscope and may tap on the subject's chest to listen for dullness. In yet another example, the caregiver or other user enters a deemed indication of the respiratory sound ascertained into an external user interface 104 or 106.

At 200, patient symptom information is sensed or collected. There are a number of ways in which the patient symptom information can be sensed or collected. In one example, this includes information about one or both of: a subject's pleuritic chest pain 172 and a subject's hiccups 174. As an example, the subject enters an indication of the intensity (e.g., numerically) of the deemed chest pain severity into external user interface 104 or 106. In another example, the caregiver examines the subject, such as by performing a lung scan, an x-ray of the subject's chest, or questioning the subject, and thereafter enters a deemed indication of the chest pain severity into external user interface 104 or 106. In another example, a user enters an indication (e.g., numerically) of the presence, intensity, frequency, or duration of one or more hiccups into external user interface 104 or 106. In yet another example, the caregiver examines the subject, such as by questioning the subject regarding the one or more hiccups in detail and enters a deemed indication of the hiccups intensity, frequency, or duration into external user interface 104 or 106.

At 202, posture information associated with sensed thoracic impedance is sensed or collected. There are a number of ways in which such information can be sensed or collected. In one example, a subject's posture 178 is measured by a posture sensor 146. In another example, an indication of the subject's posture 178 (e.g., approximate degree incline over a horizontal reference) is entered into external user interface 104 or 106 by a user.

At 204, a base thoracic impedance threshold (Threshold$_{Base}$) is changed to an adjusted thoracic impedance threshold (Threshold$_{Adjusted}$) using one or more of: the physiologic information, the patient symptom information, and the posture information associated with thoracic impedance signals, as discussed above.

At 206, the near-DC thoracic impedance signal, the posture-compensated thoracic impedance signal, or the blood resistivity-compensated near-DC thoracic impedance signal is compared to an adjusted thoracic impedance threshold value (Threshold$_{Adjusted}$). In one example, the adjusted thoracic impedance threshold value increases the sensitivity of detecting the presence of thoracic fluid. In one example, the comparison includes determining whether the near-DC thoracic impedance signal value is less than, or substantially equal to, the adjusted thoracic impedance threshold value. Where the near-DC thoracic impedance value exceeds the adjusted thoracic impedance threshold value, no significant thoracic fluid amount is deemed present at 210, the process flow then returns to 180. Where the near-DC thoracic impedance value is less than, or substantially equal to, the adjusted thoracic impedance threshold value, a significant indication of thoracic fluid accumulation is deemed present at 208. Although the foregoing included the comparison of a near-DC thoracic impedance signal to an adjusted thoracic impedance threshold, the present systems, devices, and methods are not so limited. The use of a non-filtered, non-compensated (e.g., sensed) thoracic impedance signal, posture-compensated thoracic impedance signal, or blood resistivity-compensated thoracic impedance signal is also within the scope of the present systems, devices, and methods.

At 190, the system 100 determines the existence of whether the significant thoracic fluid amount was caused by pleural effusion or pulmonary edema, such as by using one or a combination of: at least one respiratory sound 170, a pleuritic chest pain 172, one or more hiccups 174, and a rate of change of thoracic impedance with a change in posture 178. At 192, the system 100 timely alerts the subject or the caregiver to an indication of pleural effusion or pulmonary edema. The alert may be provided in a number of ways, as discussed above. At 194, a therapy is adjusted or initiated in response to the detection of one or both of: pleural effusion and pulmonary edema at 190. As an example, the therapy is selected from a group consisting of cardiac rhythm management therapy or drug therapy. Notably, the therapy provided to the subject may differ depending on whether pleural effusion, pulmonary edema, or both are detected.

Like pulmonary edema, pleural effusion will cause a decrease in thoracic impedance due to an increase in thoracic fluid. Although pleural effusion may occur in concert with pulmonary edema, pleural effusion may occur alone. The present systems, devices, and methods provide for differentiation between pleural effusion and pulmonary edema. There are also a number of other advantages. For example, the present systems, devices, and methods may improve a sensitivity or specificity of detecting the presence of thoracic fluid in a subject. The improved sensitivity may in turn provide an earlier warning of pleural effusion or pulmonary edema as compared to a lower sensitivity system, which may be critical to managing the subject's well-being.

As mentioned above, this Detailed Description is not to be taken in a limiting sense, and the scope of various embodiments is defined only by the appended claims, along with the full range of legal equivalents to which such claims are entitled. In the appended claims, the term "including" is used as the plain-English equivalent of the term "comprising." Also, in the following claims, the terms "including" and "comprising" are open-ended, that is, a system, device, article, or process that includes elements in addition to those listed after such a term in a claim are still deemed to fall within the scope of that claim.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system for the detection of fluid in a subject, comprising:
    an implantable thoracic impedance measurement circuit, configured to sense a thoracic impedance signal from the subject;
    a processor, coupled with the thoracic impedance measurement circuit to receive the thoracic impedance signal, the processor configured to detect a pleural effusion indication including a differential indication of pleural effusion relative to pulmonary edema using the thoracic impedance signal; and
    an external user interface, coupled to the processor to receive information about the pleural effusion indication, the external user interface configured to provide a user-detectable lung fluid indication using information about the pleural effusion indication.

2. The system of claim 1, comprising at least one physiologic information device coupled to the processor, the physiologic information device configured to sense or collect physiologic information about the subject.

3. The system of claim 2, wherein the processor is configured to detect the pleural effusion indication using, at least in part, the physiologic information about the subject.

4. The system of claim 3, wherein the physiologic information about the subject includes at least one respiratory sound.

5. The system of claim 1, comprising at least one patient symptom device coupled to the processor, the patient symptom device configured to sense or collect patient symptom information about the subject.

6. The system of claim 5, wherein the processor is configured to detect the pleural effusion indication using, at least in part, the patient symptom information about the subject.

7. The system of claim 6, wherein the patient symptom information about the subject includes one or both of an indication of pleuritic chest pain or at least one hiccup.

8. The system of claim 1, comprising a posture sensor coupled to the processor, the posture sensor configured to sense a posture signal indicative of the subject's then-current orientation.

9. The system of claim 8, wherein the processor is configured to detect the pleural effusion indication using, at least in part, a rate of change in the thoracic impedance signal associated with a change in the posture signal.

10. The system of claim 1, wherein the external user interface includes a user input device, the user input device configured to collect from a user one or a combination of physiologic information, patient symptom information, or posture information about the subject.

11. The system of claim 10, wherein the external user interface is configured to transmit the physiologic information, the patient symptom information, or the posture information to the processor for use in detecting the pleural effusion indication.

12. The system of claim 1, comprising a therapy control module configured to adjust or initiate a therapy using at least one of the pleural effusion indication or the user-detectable lung fluid indication.

13. A method for the detection of thoracic fluid in a subject, comprising:
   sensing a thoracic impedance signal using an implantable device;
   detecting a pleural effusion indication, including a differential indication of pleural effusion relative to pulmonary edema, using the thoracic impedance signal;
   deriving a user-detectable lung fluid indication using information about the pleural effusion indication; and
   providing the user-detectable lung fluid indication by way of an external user interface.

14. The method of claim 13, comprising sensing or receiving physiologic information about the subject, and using the physiologic information to detect the pleural effusion indication.

15. The method of claim 14, wherein sensing or receiving physiologic information about the subject includes sensing or receiving at least one respiratory sound.

16. The method of claim 13, comprising sensing or receiving patient symptom information about the subject, and using the patient symptom information to detect the pleural effusion indication.

17. The method of claim 16, wherein sensing or receiving patient symptom information about the subject includes sensing or receiving one or both of an indication of pleuritic chest pain or at least one hiccup.

18. The method of claim 13, comprising sensing or receiving a then-current posture orientation of the subject, and using information about a change in the thoracic impedance signal with a change in the posture orientation to detect the pleural effusion indication.

19. The method of claim 13, comprising filtering the thoracic impedance signal to obtain a near-DC thoracic impedance signal, and using the near-DC thoracic impedance signal to detect the pleural effusion indication.

20. The method of claim 13, comprising compensating the thoracic impedance signal to extract a blood resistivity-influenced component of the thoracic impedance signal, and using a blood resistivity-compensated thoracic impedance signal to detect the pleural effusion indication.

21. The method of claim 13, comprising providing a therapy to the subject in response to at least one of the pleural effusion indication or the user-detectable lung fluid indication.

* * * * *